United States Patent
Brodbeck et al.

(10) Patent No.: US 6,673,767 B1
(45) Date of Patent: Jan. 6, 2004

(54) GEL COMPOSITION AND METHODS

(75) Inventors: Kevin J. Brodbeck, Palo Alto, CA (US); Ann T. Gaynor-Duarte, Oakland, CA (US); Theodore Tao-Ian Shen, Redwood City, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/532,337

(22) Filed: Mar. 21, 2000

Related U.S. Application Data

(62) Division of application No. 08/993,208, filed on Dec. 18, 1997, now Pat. No. 6,130,200.
(60) Provisional application No. 60/033,439, filed on Dec. 20, 1996.

(51) Int. Cl.[7] .......................... A61K 38/27; A61K 47/30
(52) U.S. Cl. .................. 514/2; 514/772.3; 514/777; 424/422; 424/423; 424/426; 424/486; 424/487; 424/488; 604/51; 604/891.1; 604/48; 604/49; 530/399; 530/351
(58) Field of Search .................. 514/2, 772.3, 777; 424/422, 423, 426, 486, 487, 488; 604/51, 891.1, 48, 49; 530/399, 351

(56) References Cited

U.S. PATENT DOCUMENTS

| | | | |
|---|---|---|---|
| 3,636,956 A | * 1/1972 | Schneider ................... 606/224 |
| 3,714,228 A | * 1/1973 | Massie ........................ 560/106 |
| 3,792,010 A | 2/1974 | Wasserman et al.d . 260/32.2 R |
| 3,923,939 A | 12/1975 | Baker et al. ................... 264/49 |
| 4,675,189 A | 6/1987 | Kent et al. ................... 424/290 |
| 4,708,861 A | * 11/1987 | Popescu et al. .............. 424/1.1 |
| 4,938,763 A | 7/1990 | Dunn et al. ............... 604/891.1 |
| 4,962,091 A | 10/1990 | Eppstein et al. ................ 514/2 |
| 4,981,696 A | 1/1991 | Loomis et al. .............. 424/423 |
| 5,019,400 A | 5/1991 | Gombotz et al. ........... 424/497 |
| 5,077,049 A | 12/1991 | Dunn et al. ................. 424/426 |
| 5,085,866 A | 2/1992 | Consar et al. .............. 424/481 |
| 5,192,741 A | 3/1993 | Orsolini et al. ................ 514/4 |
| 5,227,157 A | 7/1993 | McGinity et al. ......... 424/78.02 |
| 5,242,910 A | * 9/1993 | Damanj ...................... 514/152 |
| 5,278,201 A | 1/1994 | Dunn et al. ................. 523/113 |
| 5,278,202 A | 1/1994 | Dunn et al. ................. 523/113 |
| 5,292,782 A | 3/1994 | Bastioli et al. ............... 524/47 |
| 5,318,780 A | 6/1994 | Viegas et al. ............... 424/427 |
| 5,324,519 A | 6/1994 | Dunn et al. ................. 424/426 |
| 5,340,849 A | 8/1994 | Dunn et al. ................. 523/113 |
| 5,358,475 A | 10/1994 | Mares et al. .................. 623/66 |
| 5,368,859 A | 11/1994 | Dunn et al. ................. 424/426 |
| 5,447,725 A | 9/1995 | Damani et al. ............. 424/435 |
| 5,487,897 A | 1/1996 | Polson et al. ............... 424/426 |
| 5,525,646 A | 6/1996 | Lundgren et al. ........... 523/105 |
| 5,556,905 A | 9/1996 | Frappier et al. ............. 524/311 |
| 5,599,552 A | 2/1997 | Dunn et al. ................. 424/423 |
| 5,620,700 A | * 4/1997 | Berggren et al. ........... 424/435 |
| 5,632,727 A | 5/1997 | Tipton et al. ................. 602/47 |
| 5,633,002 A | 5/1997 | Stricker et al. ............. 424/426 |
| 5,650,173 A | 7/1997 | Ramstack et al. .......... 424/489 |
| 5,654,010 A | 8/1997 | Johnson et al. ............. 424/502 |
| 5,656,297 A | 8/1997 | Bernstein et al. ........... 424/484 |
| 5,660,849 A | 8/1997 | Polson et al. ............... 424/426 |
| 5,667,808 A | 9/1997 | Johnson et al. ............. 424/501 |
| 5,674,534 A | 10/1997 | Zale et al. ................... 424/501 |
| 5,681,873 A | 10/1997 | Norton et al. .............. 523/115 |
| 5,702,716 A | 12/1997 | Dunn et al. ................. 424/422 |
| 5,707,647 A | 1/1998 | Dunn et al. ................. 424/443 |
| 5,711,968 A | 1/1998 | Tracy et al. ................. 424/487 |
| 5,716,644 A | 2/1998 | Zale et al. ................... 424/497 |
| 5,717,030 A | 2/1998 | Dunn et al. ................. 523/111 |
| 5,725,491 A | 3/1998 | Tipton et al. ................. 602/43 |
| 5,733,566 A | 3/1998 | Lewis ........................ 424/426 |
| 5,733,567 A | 3/1998 | Arola et al. ................. 424/426 |
| 5,842,150 A | 11/1998 | Renberg et al. .............. 702/23 |
| 6,130,200 A | 10/2000 | Brodbeck et al. .............. 514/2 |

FOREIGN PATENT DOCUMENTS

| | | | |
|---|---|---|---|
| DE | 3635679 A1 | 5/1988 | ............ A61L/17/00 |
| EP | 0 539 751 A1 | 5/1993 | ............ A61K/9/00 |
| EP | 0 640 647 A2 | 3/1995 | ............ C08L/5/08 |
| WO | WO 90/03768 | 4/1990 | ............ A61F/2/00 |
| WO | WO 91/05544 | 5/1991 | ............ A61K/9/00 |
| WO | WO 92/00718 | 1/1992 | ............ A61K/6/00 |
| WO | WO 93/20134 | 10/1993 | ............ C08K/5/00 |
| WO | WO 95/27481 | 10/1995 | ............ A61K/9/22 |
| WO | WO 96/21427 | 7/1996 | ............ A61K/9/00 |
| WO | WO 97/15285 | 5/1997 | ............ A61K/9/00 |
| WO | WO 97/15287 | 5/1997 | ............ A61K/9/10 |
| WO | WO 97/26015 | 7/1997 | |
| WO | WO 98/07412 | 2/1998 | ............ A61K/9/16 |

OTHER PUBLICATIONS

Ywey, G. L. Duysen, E.G., Cox, S. M., and Dunn, R.L., Chapter 3, "Delivery of Proteins from a Controlled Release Injectable Implant," pp. 93–117, *Protein Delivery: Physical Systems*, Sanders and Hendren, eds., Plenum Press, New York, 1997.

Modern Plasitcs Encyclopedia, pp. C99–C109, mid–Nov. 1996.

Nema, S., Washkuhn, R.J., and Brendel, R.J., "Excipients and Their Use in Injectable Products," PDA J. Pharm. Sci. Technol. (United States.) Jul.–Aug. 1997, 51 (4), pp. 166–171.

Scotchford, C.A., et al., "Water uptake and protein release characteristics of a new methacrylate–based polymer systems," Polymer, vol. 38, No. 15, pp. 3869–374, 1997.

(List continued on next page.)

*Primary Examiner*—Francisco Prats
(74) *Attorney, Agent, or Firm*—Vandana Date

(57) ABSTRACT

Methods and compositions for systemically or locally administering by implantation a beneficial agent to a subject are described, and include, for example, compositions having burst indices of 8 or less for systemic applications and systems releasing 10% or less of the total dose of beneficial agent in the first 24 hours after implantation for local applications. The compositions include a biocompatible polymer, a biocompatible solvent having low water miscibility that forms a viscous gel with the polymer and limits water uptake by the implant, and a beneficial agent.

81 Claims, 4 Drawing Sheets

OTHER PUBLICATIONS

Johnson, M. L., Jaworowicz, W., Cleland J. L., Bailey, L., Charnis, M., Duenas, E., Wu, C., Shepard, D., Magil, S., Last, T., Jones, A.J.S., and Putney, S. D., "The Stabilizaton and Encapsulation of Human Growth Hormone into Biodegradble Microspheres," Pharm. Res., vol. 14, No. 6, 1997.

Search Report of WO 98/27962, filed Jul. 2, 1998, published Oct. 15, 1998, Brodbeck, K. J. et al.

Search Report of WO 98/27963, filed Jul. 2, 1998, published Oct. 15, 1998, Brodbeck, K. J. et al.

Cunningham, B.C., Mulkerrin, M G., Wells, J. A., "Dimerization of Human Growth Hormone by Zinc," Science, vol. 253, pp. 545–548, 1991.

Derwent Abstract (English language) of DE 3635679 A (listed in Foreign Documents above).

Sato T., Kanke, M., Schroeder, H. G., and DeLuca, P.P., "Porous Biodegradable Microspheres for Controlled Drug Delivery. I. Assessment of Processing Conditions and Solvent Removal Techniques," Pharm. Res. vol. 5, No. 1, pp. 21–30, 1997.

Zhang, Y., Zale, S., Sawyer, L., and Bernstein, AH., "Effects of metal salts on poly(DL–lactide–co–glycolide) polymer hydrolysis," J. Biomedical Materials Research, vol. 34, 531–538, 1997.

\* cited by examiner

GEL COMPOSITION AND METHODS

CROSS REFERENCE TO RELATED APPLICATIONS

This application is a divisional of U.S. application Ser. No. 08/993,208 filed Dec. 18, 1997 now U.S. Pat. No. 6,130,200.

This application claims the priority of provisional application Ser. No. 60/033,439, filed Dec. 20, 1996, which is incorporated herein by reference.

BACKGROUND OF THE INVENTION

1. Field of the Invention

The present invention relates to a gel composition that can be implanted into a desired location and which can provide controlled release of a beneficial agent. The present invention also relates to methods of controlling release of a beneficial agent from a composition.

2. Description of the Related Art

Biodegradable polymers have been used for many years in medical applications. Illustrative devices composed of the biodegradable polymers include sutures, surgical clips, staples, implants, and sustained release drug delivery systems. The majority of these biodegradable polymers have been based upon glycolide, lactide, caprolactone, and copolymers thereof.

The biodegradable polymers can be thermoplastic materials which means that they can be heated and formed into various shapes such as fibers, clips, staples, pins, films, etc. Alternatively, they can be thermosetting materials formed by crosslinking reactions which lead to high-molecular-weight materials that do not melt or form flowable liquids at high temperatures.

Although thermoplastic and thermosetting biodegradable polymers have many useful biomedical applications, there are several important limitations to their use in the bodies of various animals including humans, animals, birds, fish, and reptiles. Because these polymers generally are solids, all instances involving their use have required initially forming the polymeric structures outside the body, followed by insertion of the solid structure into the body. For example, sutures, clips, and staples are all formed from thermoplastic biodegradable polymers prior to use. When inserted into the body, they retain their original shape. While this characteristic is essential for some uses, it is not preferred where it is desired that the material be molded or flow to fill voids or cavities where it may be most needed.

Drug delivery systems using thermoplastic or thermosetting biodegradable polymers also often are or have to be formed outside the body. In such instances, the drug is incorporated into the polymer and the mixture is shaped into a certain form such as cylinder, disc, or fiber for implantation. With such solid implants, the drug delivery system has to be inserted into the body through an incision. These incisions are sometimes larger than desired by the medical profession and occasionally lead to a reluctance of the patient to accept such an implant or drug delivery system. Nonetheless, both biodegradable and non-biodegradable implantable drug delivery systems have been widely used successfully.

One reservoir device having a rate-controlling membrane and zero-order release of an agent that is particularly designed for intraoral implantation is described in U.S. Pat. No. 5,085,866. The device is prepared from a core that is sprayed with a solution having a polymer and a solvent that is composed of a rapidly evaporating, low boiling point first solvent and a slowly evaporating, high boiling point second solvent.

Other illustrative osmotic delivery systems include those disclosed in U.S. Pat. Nos. 3,797,492, 3,987,790, 4,008,719, 4,865,845, 5,057,318, 5,059,423, 5,112,614, 5,137,727, 5,151,093, 5,234,692, 5,234,693, 5,279,608, and 5,336,057. Pulsatile delivery devices are also known which deliver a beneficial agent in a pulsatile manner as disclosed in U.S. Pat. Nos. 5,209,746, 5,308,348, and 5,456,679.

One way to avoid the incision needed to implant drug delivery systems is to inject them as small particles, microspheres, or microcapsules. For example, U.S. Pat. No. 5,019,400 describes the preparation of controlled release microspheres via a very low temperature casting process. These materials may or may not contain a drug which can be released into the body. Although these materials can be injected into the body with a syringe, they do not always satisfy the demand for a biodegradable implant. Because they are particulate in nature, they do not form a continuous film or solid implant with the structural integrity needed for certain prostheses. When inserted into certain body cavities such as a mouth, a periodontal pocket, the eye, or the vagina where there is considerable fluid flow, these small particles, microspheres, or microcapsules are poorly retained because of their small size and discontinuous nature. Further, the particles tend to aggregate and thus their behavior is hard to predict. In addition, microspheres or microcapsules prepared from these polymers and containing drugs for release into the body are sometimes difficult to produce on a large scale, and their storage and injection characteristics present problems. Furthermore, one other major limitation of the microcapsule or small-particle system is their lack of reversibility without extensive surgical intervention. That is, if there are complications after they have been injected, it is considerably more difficult to remove them from the body than with solid implants. A still further limitation on microparticles or microcapsulation is the difficulty in encapsulating protein and DNA-based drugs without degradation caused by denaturing solvents and temperature extremes used during processing.

The art has developed various drug delivery systems in response to the aforementioned challenges. For instance, U.S. Pat. No. 4,938,763 and its divisional U.S. Pat. No. 5,278,201 relate to a biodegradable polymer for use in providing syringeable, in-situ forming, solid biodegradable implants for animals. In one embodiment, a thermoplastic system is used wherein a non-reactive polymer is dissolved in a water soluble biocompatible solvent to form a liquid which is placed in the animal wherein the solvent dissipates to produce the solid implant. Alternatively, a thermosetting system is used wherein effective amounts of a liquid acrylic ester-terminated, biodegradable prepolymer and a curing agent are formed and the liquid mixture is placed within the animal wherein the prepolymer cures to form the solid implant. It is stated that the systems provide a syringeable, solid biodegradable delivery system by the addition of an effective level of a biologically active agent to the liquid before the injection into the animal.

U.S. Pat. No. 5,599,552 describes thermoplastic and thermoset polymer compositions that utilize solvents which are miscible to dispersible in water, such as N-methyl-2-pyrrolidone, resulting in polymer solutions capable of quickly absorbing water from surrounding tissue. The polarity of the solvents is described as being effective to provide about at least 10% solubility in water. The polymer matrix systems are described as forming a porous core surrounded by a porous skin.

U.S. Pat. No. 5,242,910 describes a sustained release composition containing drugs for treating periodontal disease. The composition comprises copolymers of lactide and glycolide, triacetin (as a solvent/plasticizer) and an agent providing relief of oral cavity diseases. The composition can take the form of a gel and can be inserted into a periodontal cavity via a syringe using either a needle or a catheter. As additional optional components, the composition can contain surfactants, flavoring agents, viscosity controlling agents, complexing agents, antioxidants, other polymers, gums, waxes/oils, and coloring agents. One illustrative viscosity controlling agent set forth in one of the examples is polyethylene glycol 400.

U.S. Pat. No. 5,620,700 describes a polymer-drug matrix, optionally including plasticizers in an amount up to about 30 wt %, for local application of drug in the peridontal cavity. Among the plasticizers listed are, inter alia, triethyl citrate, acetyl triethyl citrate, tributyl citrate, acetyl tributyl citrate, diethyl phthalate, diethyl tartrate, ethyl lactate, triacetin and diacetin. The polymer matrix is non-flowable prior to administration and is heated to become flowable so that it may be dispensed into the peridontal cavity where it solidifies. While the patent discusses possible systemic applications by delivery via the ocular sacs of the eye or intravaginal delivery, it does not address the issue of burst of drug or methods of controlling burst.

U.S. Pat. No. 3,923,939 describes a method of reducing initial burst of an active agent from a delivery device by removing, prior to implantation, active agent from the exterior surface of the delivery device and through a layer of at least 5% of the overall body thickness extending from the exterior surface of the device.

U.S. Pat. No. 5,556,905 describes degradable thermoplastic compositions which are modified by plasticizers consisting of various partial esters of citric acid.

Prior art polymer compositions for injectable implants have used solvent/plasticizers that are very or relatively soluble in aqueous body fluids to promote rapid solidification of the polymer at the implant site and promote diffusion of drug from the implant. However, it has now been observed that a serious problem associated with prior art polymeric implants utilizing water soluble polymer solvents is the rapid migration of water into the polymer composition when the implant is placed in the body and exposed to aqueous body fluids. That characteristic often results in uncontrolled release of beneficial agent that is manifested by an initial, rapid release of beneficial agent from the polymer composition, corresponding to a "burst" of beneficial agent being released from the implant. The burst often results in a substantial portion of the beneficial agent, if not all, being released in a very short time, e.g., hours or 1–2 days. Such an effect can be unacceptable, particularly in those circumstances where sustained delivery is desired, i.e., delivery of beneficial agent over a period of a week or a month or more, or where there is a narrow therapeutic window and release of excess beneficial agent can result in adverse consequences to the subject being treated, or where it is necessary to mimic the naturally-occurring daily profile of beneficial agents, such as hormones and the like, in the body of the subject being treated.

In an attempt to control burst and modulate and stabilize the delivery of the beneficial agent the prior art has coated particles of beneficial agent to retard release into an aqueous environment and extend release of the beneficial agent over time. Alternatively, various stabilizing or release modulating agents, such as metal salts as described in U.S. Pat. Nos. 5,656,297; 5,654,010; 4,985,404 and 4,853,218 have been used. Notwithstanding some success, those methods have not been entirely satisfactory for the large number of beneficial agents that would be effectively delivered by implants, since in many instances the modulation and stabilization effect is the result of the formation of a complex of the metal ion with the beneficial agent. When such complexes do not form, the stabilization/modulation effect may not be adequate to prevent undesirable "burst" of the beneficial agent upon its introduction into the implant site.

Additionally, with conventional low viscosity, solvent-based depot compositions comprised of a polymer dissolved in a solvent, another problem which often exists is that the composition solidifies slowly after injection as solvent diffuses from the depot and water migrates into the depot. Since these compositions are relatively non-viscous in order to be injected, a large percentage of drug may be rapidly released as the system forms by diffusion of the solvent, particularly when the beneficial agent is soluble in the solvent and the solvent rapidly disperses into body fluids. Rapid solvent release contributes to the "burst" effect along with depot hardening due to water uptake. In this respect, it is typical for conventional solvent-based compositions to have a drug burst wherein 30–75% of the drug contained in the composition is released within one day of the initial injection.

The rapid water uptake into the polymer implant and solvent dispersion into body fluids exhibited by prior art devices often results in implants having pore structures that are non-homogeneous in size and shape. Typically, the surface pores take on a finger-like pore structure extending for as much as ⅓ of a millimeter or more from the implant surface into the implant, and such finger-like pores are open at the surface of the implant to the environment of use. The internal pores tend to be smaller and less accessible to the fluids present in the environment of use. Accordingly, when such devices are implanted, the finger-like pores allow very rapid uptake of aqueous body fluids into the interior of the implant with consequent immediate and rapid dissolution of significant quantities of beneficial agent and unimpeded diffusion of beneficial agent into the environment of use, producing the burst effect discussed above.

Furthermore, rapid water uptake can result in premature polymer precipitation such that a hardened implant or one with a hardened skin is produced. The inner pores and much of the interior of the polymer containing beneficial agent are shut off from contact with the body fluids and a significant reduction in the release of beneficial agent can result over a not insignificant period of time ("lag time"). That lag time is undesirable from the standpoint of presenting a controlled, sustained release of beneficial agent to the subject being treated. What one observes, then, is a burst of beneficial agent being released in a short time period immediately after implantation, a lag time in which no or very little beneficial agent is being released, and subsequently continued delivery of beneficial agent (assuming beneficial agent remains after the burst) until the supply of beneficial agent is exhausted.

SUMMARY OF THE INVENTION

The present invention provides a method and an implantable system for systemic and local delivery of a beneficial agent to a subject. The method and system provide controlled release of beneficial agent to the subject being treated and limit the initial burst of beneficial agent from the implant system. Additionally, the invention provides a method of preparing implant systems having restricted initial burst of beneficial agent.

In one aspect, the invention comprises a method of administering, locally or systemically, a beneficial agent to a subject which comprises implanting a system comprising a beneficial agent dispersed or dissolved substantially throughout a viscous gel, the system releasing 20% or less by weight of the beneficial agent present in the viscous gel within the first 24 hours after implantation in the subject. Preferably, 10% or less by weight of the beneficial agent will be released within the first 24 hours after implantation.

In another aspect, the invention comprises a method of systemically administering a beneficial agent to a subject which comprises implanting a system comprising a beneficial agent dispersed or dissolved substantially throughout a viscous gel, the system having a burst index of 8 or less.

In still another aspect, the invention comprises a method of systemically administering a beneficial agent to a subject in a controlled manner approximating zero order release by implanting a gel composition comprising a biocompatible polymer, a biocompatible solvent having a solubility in water of less than 7% and forming a viscous gel with the polymer, and a beneficial agent, wherein the loading of the beneficial agent in the interior of the polymer gel is above that required to saturate the beneficial agent in water.

In still another aspect, the invention comprises an implantable, biodegradable composition for the systemic delivery of a beneficial agent to a subject wherein the composition comprises a polymer; an amount of a solvent to form a viscous gel with the polymer, and a beneficial agent dissolved or dispersed in the gel, wherein the solvent comprises a single solvent or a mixture of solvents with at least one solvent having a miscibility in water of less than 7% by weight and the amount of solvent constituting 40% or more by weight of the gel vehicle.

In a further aspect, the present invention comprises an implantable, biodegradable composition for the sustained delivery of a beneficial agent to a subject wherein the composition comprises a polymer; an effective plasticizing amount of a solvent to form a viscous gel with the polymer; and a beneficial agent dissolved or dispersed in the gel, wherein the solvent comprises a mixture of solvents with at least one solvent in the mixture having a miscibility in water of less than 7% by weight. Preferably, the miscibility in water of the solvent mixture is 20% or less by weight, and more preferably 10% or less by weight.

In yet another aspect, the invention comprises an implantable, biodegradable composition for delivery of a beneficial agent to a subject wherein the composition comprises a polymer; an effective plasticizing amount of a solvent to form a viscous gel with the polymer; and a beneficial agent dissolved or dispersed in the gel, wherein the solvent comprises a single solvent or a mixture of solvents with at least one solvent having a miscibility in water of less than 7% by weight selected from lower alkyl and aralkyl esters of benzoic acid.

In another aspect the present invention provides an implantable gel composition for systemic delivery of a beneficial agent to a subject comprising:

A) a biocompatible polymer;
B) a biocompatible solvent, having miscibility in water of less than 7% by weight and capable of dissolving the polymer and forming a viscous gel, said solvent being selected from the group comprising compounds having the following structural formula:

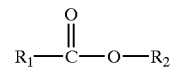

and

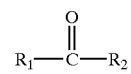

wherein $R_1$ is lower alkyl, aryl or aralkyl and $R_2$ is aralkyl or lower alkyl; and $R_1$ and $R_2$ may be the same or different; with the proviso that when $R_1$ and $R_2$ are each lower alkyl, the number of total carbon atoms represented by $R_1$ and $R_2$ combined is 4 or more;

C) a beneficial agent; and, optionally, one or more of the following:
D) an emulsifying agent;
E) a pore former;
F) a solubility modulator of the beneficial agent; and
G) an osmotic agent.

In another aspect the present invention provides an implantable gel composition comprising:

A) a biocompatible polymer;
B) a biocompatible solvent having miscibility in water of less than 7% by weight and capable of dissolving the polymer and forming a viscous gel, said solvent being selected from the group comprising compounds having the following structural formula:

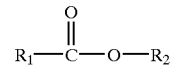

wherein $R_1$ and $R_2$ are as defined above.

In a further aspect, the present invention provides a method of restricting uptake of water by a gel composition which comprises forming the gel composition from a polymer and a solvent that forms a viscous gel with the polymer, the solvent having a miscibility in water of less than 7% by weight. Preferably, the solvent will have a miscibility in water of 6% or less by weight, and more preferably 5% or less by weight.

In another aspect, the present invention provides a method of preparing an injectable gel composition comprising:

A) mixing a biocompatible polymer and a solvent having a miscibility in water of 7% or less selected from lower alkyl and aralkyl esters of benzoic acid to form a viscous gel;
B) dispersing or dissolving a beneficial agent, optionally associated with a solubility modulator of the beneficial agent, in an emulsifying agent to form a beneficial agent containing emulsifying agent; and
C) mixing the beneficial agent containing emulsifying agent with the viscous gel, said beneficial agent containing emulsifying agent forming a dispersed droplet phase in the viscous gel, and optionally,
D) mixing one or more of a pore former and an osmotic agent with said viscous gel.

In another aspect, the present invention provides a method of preparing an implantable gel composition comprising:

A) mixing a biocompatible polymer and a solvent having a miscibility in water of 7% or less selected from lower alkyl and aralkyl esters of benzoic acid to form a viscous gel;

B) dispersing or dissolving a beneficial agent, optionally associated with a solubility modulator of the beneficial agent, in the viscous gel; and;

C) optionally mixing one or more of the following: an emulsifying agent, a pore former, a solubility modulator of the beneficial agent and an osmotic agent, with the beneficial agent containing gel.

In yet another aspect, the invention provides a gel composition comprising:

A) a biocompatible polymer;

B) a biocompatible solvent having a miscibility in water of less than 7% by weight;

C) a beneficial agent selected from the group consisting of cDNA, DNA, peptides, proteins and fragments and derivatives thereof, and optionally, one or more of the following:

D) an emulsifying agent;

E) a pore former;

F) a solubility modulator of the beneficial agent; and

G) an osmotic agent;

wherein the composition has a burst index of less than 8.

In still another aspect, the invention comprises a kit for administration of a beneficial agent to a subject comprising:

A) a biocompatible polymer;

B) a solvent having a miscibility in water of 7% or less by weight that is suitable for dissolving the polymer and forming a viscous gel;

C) a beneficial agent; and optionally, one or more of the following:

D) an emulsifying agent;

E) a pore former;

F) a solubility modulator of the beneficial agent, optionally associated with the beneficial agent; and G) an osmotic agent;

wherein at least the beneficial agent, optionally associated with the solubility modulator, is maintained separated from the solvent until the time of administration of the beneficial agent to a subject.

In still another aspect, the invention comprises an implantable composition for the systemic delivery of a beneficial agent comprising a poly(lactide-co-glycolide) copolymer; an effective plasticizing amount of a solvent to form a viscous gel with the polymer; and a beneficial agent selected from the group consisting of cDNA, DNA, peptides, proteins and fragments and derivatives thereof, said composition having a burst index of 8 or less.

In another aspect, the invention comprises an implantable composition for the sustained delivery of a beneficial agent comprising a poly(lactide-co-glycolide) copolymer; an effective plasticizing amount of a solvent selected from lower alkyl and aralkyl esters of benzoic acid to form a viscous gel with the polymer; and a beneficial agent.

In a further aspect, the invention comprises an implantable composition comprising a viscous gel and a beneficial agent dispersed or dissolved therein, wherein the viscous gel maintains a glass transition temperature of less than 37° C. for at least the first 24 hours after implantation.

In yet another aspect, the invention comprises a method of administering a beneficial agent to a subject which comprises implanting a system comprising a beneficial agent dissolved or dispersed substantially throughout a viscous gel formed of a biocompatible polymer and a solvent having a solubility in water of 7% or less, and a solubility modulator of the beneficial agent, the system having a burst index of 8 or less.

In a further aspect, the invention comprises an implantable system comprising a beneficial agent dissolved or dispersed substantially throughout a viscous gel formed of a biocompatible polymer and a solvent having a solubility in water of 7% or less, and a solubility modulator of the beneficial agent, the system having a burst index of 8 or less.

BRIEF DESCRIPTION OF THE DRAWINGS

The foregoing and other objects, features and advantages of the present invention will be more readily understood upon reading the following detailed description in conjunction with the drawings in which.

DETAILED DESCRIPTION OF THE INVENTION

Figure 1:
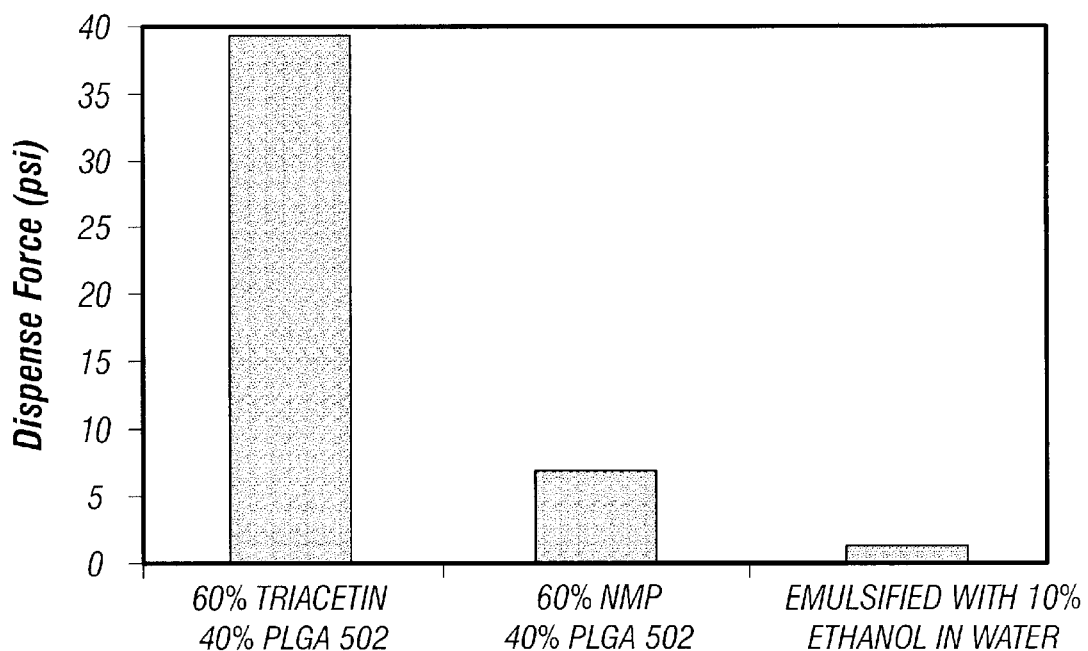
FIG. 1 is a graph illustrating the dispense force required to dispense emulsified and non-emulsified viscous gel compositions through a 20 gauge needle in psig at 2 cc/min.

The present invention is directed to a method of systemically or locally administering a beneficial agent to a subject by implanting in the subject an implantable system, formed as a viscous gel from a biocompatible polymer and a biocompatible solvent, and a beneficial agent is substantially dissolved or dispersed throughout the gel. By appropriate choice of solvent, water migration from the aqueous environment surrounding the implant system is restricted, and beneficial agent is released to the subject over a prolonged period of time, thus providing for delivery of the beneficial agent with a controlled burst of beneficial agent and sustained release thereafter.

It has been discovered that when a solvent having a solubility in water of less than 7% by weight in water is present in the system, suitable burst control and sustained delivery of beneficial agent is achieved, whether or not a solubility modulator of the beneficial agent is present in the system. Typically, the implant systems useful in this invention will release, in the first 24 hours after implantation, 20% or less of the total amount of beneficial agent to be delivered to the subject from the implant system, preferably 15% or less and more preferably 10% or less. The viscous gel formed preferably is bioerodible so that the implant system does not have to be surgically removed after beneficial agent is depleted from the implant.

Water uptake and burst may be controlled by using polymer-solvent compositions wherein the solvent is substantially immiscible in water, i.e., less than 7% by weight soluble in water, so as to control the rate of water migration into the polymer implant and ultimately control the burst of beneficial agent and the sustained delivery of beneficial agent. Generally, the compositions of the invention will be gel-like and will form with a substantially homogeneous pore structure throughout the implant upon implantation and during drug delivery, even as it hardens. Furthermore, while the polymer gel implant will slowly harden when subjected to an aqueous environment, the hardened implant may maintain a rubbery (non-rigid) composition with the glass transition temperature being below 37° C.

Since the compositions often will be highly viscous prior to implantation, when the composition is intended for implantation by injection, the viscosity optionally may be modified by emulsifiers to obtain a gel composition having a viscosity low enough to permit passage of the gel composition through a needle. Also, pore formers and solubility modulators of the beneficial agent may be added to the implant systems to provide desired release profiles from the implant systems, along with typical pharmaceutical excipients and other additives that do not change the beneficial aspects of the present invention. The addition of a solubility modulator to the implant system may enable the use of a solvent having a solubility of 7% or greater in the implant system with minimal burst and sustained delivery under particular circumstances. However, it is presently preferred that the implant system utilize at least one solvent having a solubility in water of less than 7% by weight, whether the solvent is present alone or as part of a solvent mixture. It has also been discovered that when mixtures of solvents which include a solvent having 7% or less by weight solubility in water and one or more miscible solvents, optionally having greater solubility, are used, implant systems exhibiting limited water uptake and minimal burst and sustained delivery characteristics are obtained.

Definitions

The term "beneficial agent" means an agent that effects a desired beneficial, often pharmacological, effect upon administration to a human or an animal, whether alone or in combination with other pharmaceutical excipients or inert ingredients.

The term "AUC" means the area under the curve obtained from an in vivo assay in a subject by plotting blood plasma concentration of the beneficial agent in the subject against time, as measured from the time of implantation of the composition, to a time "t" after implantation. The time t will correspond to the delivery period of beneficial agent to a subject.

The term "burst index" means, with respect to a particular composition intended for systemic delivery of a beneficial agent, the quotient formed by dividing (i) the AUC calculated for the first twenty-four hours after implantation of the composition into a subject divided by the number 24, by (ii) the AUC calculated for the time period of delivery of beneficial agent, divided by the number of hours in the total duration of the delivery period.

The phrase "dissolved or dispersed" is intended to encompass all means of establishing a presence of beneficial agent in the gel composition and includes dissolution, dispersion, suspension and the like.

The term "systemic" means, with respect to delivery or administration of a beneficial agent to a subject, that beneficial agent is detectable at a biologically-significant level in the blood plasma of the subject.

The term "local" means, with respect to delivery or administration of a beneficial agent to a subject, that beneficial agent is delivered to a localized site in the subject but is not detectable at a biologically-significant level in the blood plasma of the subject.

The term "gel vehicle" means the composition formed by mixture of the polymer and solvent in the absence of the beneficial agent.

The term "prolonged period" means a period of time over which release of a beneficial agent from the implant of the invention occurs, which will generally be about one week or longer, and preferably about 30 days or longer.

The term "initial burst" means, with respect to a particular composition of this invention, the quotient obtained by dividing (i) the amount by weight of beneficial agent released from the composition in a predetermined initial period of time after implantation, by (ii) the total amount of beneficial agent that is to be delivered from an implanted composition. It is understood that the initial burst may vary depending on the shape and surface area of the implant. Accordingly, the percentages and burst indices associated with initial burst described herein are intended to apply to compositions tested in a form resulting from dispensing of the composition from a standard syringe.

The term "solubility modulator" means, with respect to the beneficial agent, an agent that will alter the solubility of the beneficial agent, with reference to polymer solvent or water, from the solubility of beneficial agent in the absence of the modulator. The modulator may enhance or retard the solubility of the beneficial agent in the solvent or water. However, in the case of beneficial agents that are highly water soluble, the solubility modulator will generally be an agent that will retard the solubility of the beneficial agent in water. The effects of solubility modulators of the beneficial agent may result from intereactions of the solubility modulator with the solvent, or with the beneficial agent itself, such as by the formation of complexes, or with both. For the purposes hereof, when the solubility modulator is "associated" with the beneficial agent, all such interactions or formations as may occur are intended. Solubility modulators may be mixed with the beneficial agent prior to its combination with the viscous gel or may be added to the viscous gel prior to the addition of the beneficial agent, as appropriate.

The term "subject" means, with respect to the administration of a composition of the invention, an animal or a human being.

Since all solvents, at least on a molecular level, will be soluble in water (i.e., miscible with water) to some very limited extent, the term "immiscible" as used herein means that 7% or less by weight of the solvent is soluble in or miscible with water. For the purposes of this disclosure, solubility values of solvent in water are considered to be determined at 20° C. Since it is generally recognized that solubility values as reported may not always be conducted at the same conditions, solubility limits recited herein as percent by weight miscible or soluble with water as part of a range or upper limit may not be absolute. For example, if the upper limit on solvent solubility in water is recited herein as "7% by weight", and no further limitations on the solvent are provided, the solvent "triacetin", which has a reported solubility in water of 7.17 grams in 100 ml of water, is considered to be included within the limit of 7%. A solubility limit in water of less than 7% by weight as used herein does not include the solvent triacetin or solvents having solubilities in water equal to or greater than triacetin.

The polymer, solvent and other agents of the invention must be biocompatible; that is they must not cause irritation or necrosis in the environment of use. The environment of use is a fluid environment and may comprise a subcutaneous or intramuscular portion or body cavity of a human or animal.

Polymers that may be useful in the invention may be biodegradable and may include, but are not limited to polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly (malic acid), poly(amino acids), polyvinylpyrrolidone, polyethylene glycol, polyhydroxycellulose, chitin, chitosan, and copolymers, terpolymers and mixtures thereof.

Presently preferred polymers are polylactides, that is, a lactic acid-based polymer that can be based solely on lactic acid or can be a copolymer based on lactic acid and glycolic acid which may include small amounts of other comonomers that do not substantially affect the advantageous results which can be achieved in accordance with the present invention. As used herein, the term "lactic acid" includes the isomers L-lactic acid, D-lactic acid, DL-lactic acid and lactide while the term "glycolic acid" includes glycolide. Most preferred are poly(lactide-co-glycolide)copolymers, commonly referred to as PLGA. The polymer may have a monomer ratio of lactic acid/glycolic acid of from about 100:0 to about 15:85, preferably from about 60:40 to about 75:25 and an especially useful copolymer has a monomer ratio of lactic acid/glycolic acid of about 50:50.

The lactic acid-based polymer has a number average molecular weight of from about 1,000 to about 120,000, preferably from about 5,000 to about 30,000 as determined by gas phase chromatography. As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 5,000, 10,000, 30,000 and 100,000, preferably about 8,000 to 13,000, and most preferably about 10,000, and a wide variety of end groups to alter susceptibility to hydrolysis and subsequent breakdown of the polymer chain are available from Boehringer Ingelheim (Petersburg, Va.).

The biocompatible polymer is present in the gel composition in an amount ranging from about 5 to about 80% by weight, preferably from about 30 to about 70% by weight and often 40 to 60% by weight of the viscous gel, the viscous gel comprising the combined amounts of the biocompatible polymer and the solvent. The solvent will be added to polymer in amounts described below, to provide implantable or injectable viscous gels.

The solvent must be biocompatible, should form a viscous gel with the polymer, and restrict water uptake into the implant. The solvent may be a single solvent or a mixture of solvents exhibiting the foregoing properties. The term "solvent", unless specifically indicated otherwise, means a single solvent or a mixture of solvents. Suitable solvents will substantially restrict the uptake of water by the implant and may be characterized as immiscible in water, i.e., having a solubility in water of less than 7% by weight. Preferably, the solvents are five weight percent or less soluble in water; more preferably three weight percent or less soluble in water; and even more preferably one weight percent or less soluble in water. Most preferably the solubility of the solvent in water is equal to or less than 0.5 weight percent.

Water miscibility may be determined experimentally as follows: Water (1–5 g) is placed in a tared clear container at a controlled temperature, about 20° C., and weighed, and a candidate solvent is added dropwise. The solution is swirled to observe phase separation. When the saturation point appears to be reached, as determined by observation of phase separation, the solution is allowed to stand overnight and is re-checked the following day. If the solution is still saturated, as determined by observation of phase separation, then the percent (w/w) of solvent added is determined. Otherwise more solvent is added and the process repeated. Solubility or miscibility is determined by dividing the total weight of solvent added by the final weight of the solvent/water mixture. When solvent mixtures are used, for example 20% triacetin and 80% benzyl benzoate, they are pre-mixed prior to adding to the water.

Solvents useful in this invention are generally less than 7% water soluble by weight as described above. Solvents having the above solubility parameter may be selected from the lower alkyl and aralkyl esters of aryl acids such as benzoic acid, the phthalic acids, salicylic acid, lower alkyl esters of citric acid, such as triethyl citrate and tributyl citrate and the like, and aryl, aralkyl and lower alkyl ketones. Among preferred solvents are those having solubilities within the foregoing range selected from (i) compounds having the following structural formulas:

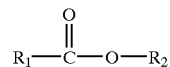

and (i)

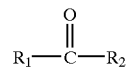

in which $R_1$ is aryl or aralkyl, $R_2$ is lower alkyl or aralkyl, and $R_1$ and $R_2$ are optionally the same or different, with the proviso that when each of $R_1$ and $R_2$ are lower alkyl, the total carbon atoms in $R_1$ and $R_2$ combined are 4 or more, and (ii) lower alkyl and aralkyl esters of phthalic acid, isophthalic acid and terephtalic acid and (iii) lower alkyl and aralkyl esters of citric acid. For the purposes hereof, lower alkyl means straight or branched chain hydrocarbons having 1–6 carbon atoms, optionally substituted with non-interfering substituents; aralkyl means (lower alkyl)phenyl, e.g., benzyl, phenethyl, 1-phenylpropyl, 2-phenylpropyl, and the like wherein the alkyl moiety contains from 1–6 carbon atoms; and aryl means phenyl, optionally substituted by non-interfering substituents. Many of the solvents useful in the invention are available commercially (Aldrich Chemicals, Sigma Chemicals) or may be prepared by conventional esterification of the respective arylalkanoic acids using acid halides, and optionally esterification catalysts, such as described in U.S. Pat. No. 5,556,905, which is incorporated herein by reference, and in the case of ketones, oxidation of their respective secondary alcohol precursors.

Art recognized benzoic acid derivatives from which solvents having the requisite solubility may be selected include: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, iso decyl benzoate, neopentyl glycol dibenzoate, glyceryl tribenzoate, pentaerylthritol tetrabenzoate, cumylphenyl benzoate, trimethyl pentanediol dibenzoate.

Art recognized phthalic acid derivatives from which solvents having the requisite solubility may be selected include: Alkyl benzyl phthalate, bis-cumyl-phenyl isophthalate, dibutoxyethyl phthalate, dimethyl phthalate, dimethyl phthalate, diethyl phthalate, dibutyl phthalate, diisobutyl phthalate, butyl octyl phthalate, diisoheptyl phthalate, butyl octyl phthalate, diisonoyl phthalate, nonyl undecyl phthalate, dioctyl phthalate, di-iso octyl phthalate, dicapryl phthalate, mixed alcohol phthalate, di-(2-ethylhexyl) phthalate, linear heptyl, nonyl, phthalate, linear heptyl, nonyl, undecyl phthalate, linear nonyl phthalate, linear nonyl undecyl phthalate, linear dinoyl, didecyl phthalate (diisodecyl phthalate), diundecyl phthalate, ditridecyl phthalate, undecyldodecyl phthalate, decyltridecyl phthalate, blend ($^{50}/_{50}$) of dioctyl and didecyl phthalates, butyl benzyl phthalate, and dicyclohexyl phthalate.

Preferred solvents include the lower alkyl and aralkyl esters of the aryl acids described above. Representative acids are benzoic acid and the phthalic acids, such as phthalic acid, isophthalic acid, and terephathalic acid. Most preferred solvents are derivatives of benzoic acid and include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred. Preferred solvent mixtures are those in which benzyl benzoate is the primary solvent, and mixtures formed of benzyl benzoate and either triacetin, tributyl citrate, triethyl citrate or N-methyl-2-pyrrolidone. Preferred mixtures are those in which benzyl benzoate is present by weight in an amount of 50% or more, more preferably 60% or more and most preferably 80% or more of the total amount of solvent present. Especially preferred mixtures are those of $^{80}/_{20}$ mixtures by weight of benzyl benzoate/triacetin and benzyl benzoate/N-methyl-2-pyrrolidone.

It has been surprisingly found that the solvents described above having a miscibility in water of less than 7% by weight may be mixed with one or more additional miscible solvents ("component solvents"). Component solvents compatible and miscible with the primary solvent may have a higher miscibility with water and the resulting mixtures may still exhibit significant restriction of water uptake into the implant. Such mixtures will be referred to as "component solvent mixtures." Useful component solvent mixtures may exhibit solubilities in water greater than the primary solvents themselves, typically between 0.1 weight percent and up to and including 50 weight percent, preferably up to and including 30 weight percent, and most preferably up to an including 10 weight percent, without detrimentally affecting the restriction of water uptake exhibited by the implants of the invention. Especially preferred are component solvent mixtures having a solubility in water of about 0.1% to about 7% by weight.

Component solvents useful in component solvent mixtures are those solvents that are miscible with the primary solvent or solvent mixture, and include, but are not limited, to triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacyclo-heptan-2-one, and mixtures thereof.

In an especially preferred embodiment, the primary solvent is selected from lower alkyl and aralkyl esters of benzoic acid and the polymer is a lactic-acid based polymer, most preferably PLGA, having a number average molecular weight of between about 8,000 to about 13,000, preferably about 10,000. Presently, the most preferred solvents are benzyl benzoate and the lower alkyl esters of benzoic acid. The benzoic acid esters may be used alone or in a mixture with other miscible solvents, e.g., triacetin, as described herein. Implants are prepared as viscous gels in which the beneficial agent is dissolved or dispersed substantially throughout, and such compositions are useful both for systemic and local administration of beneficial agent, whether or not initial burst is an important consideration. Additionally, use of esters of benzoic acid provides increased control of water migration resulting in increased stability of beneficial agent. The low water uptake, i.e., limited water migration into the gel composition after implantation, permits the practitioner of the invention to limit beneficial agent transfer by diffusion and enhance control of the delivery profile of the beneficial agent by controlling the bioerosion characteristics of the polymer. The preferred compositions allow beneficial agent to be loaded into the interior of the polymer at levels that are above that required to saturate the beneficial agent in water, thereby facilitating zero order release of beneficial agent. Additionally, the preferred compositions may provide viscous gels that have a glass transition temperature that is less than 37° C., such that the gel remains non-rigid for a period of time after implantation of 24 hours or more.

The solvent or solvent mixture is capable of dissolving the polymer to form a viscous gel that can maintain particles of the beneficial agent dissolved or dispersed and isolated from the environment of use prior to release. The compositions of the present invention provide implants having a low burst index. Water uptake is controlled by the use of a solvent or component solvent mixture that soublizes or plasticizes the polymer but substantially restricts uptake of water into implant.

Figure 4A:
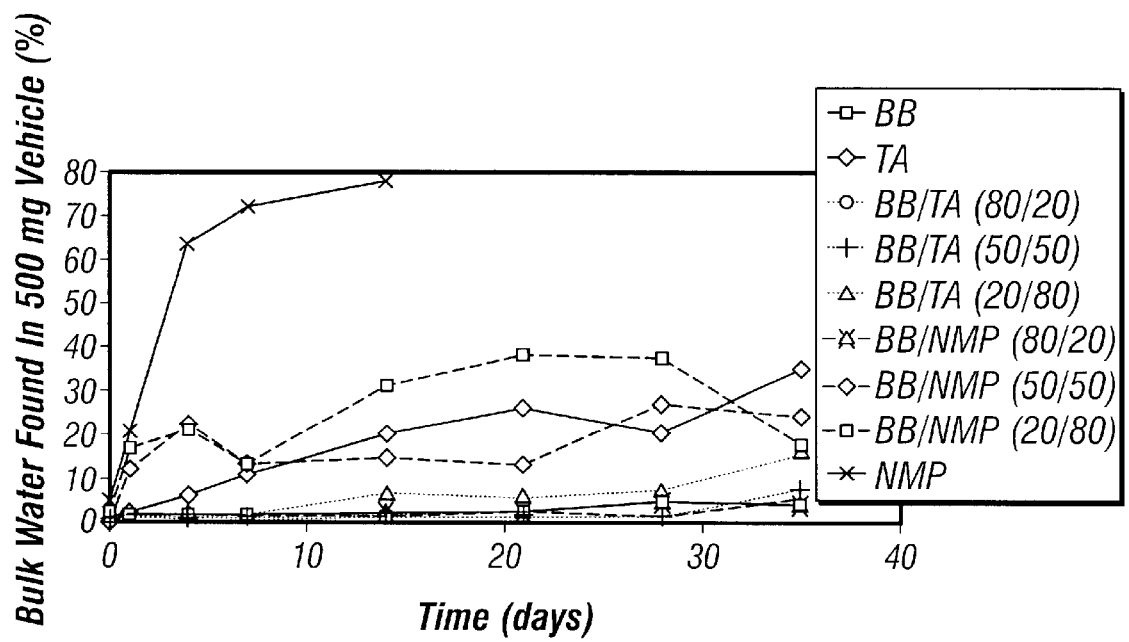
FIGS. 4A and 4B are graphs illustrating the degree of water uptake for various polymer-solvent mixtures, some of which form a part of this invention, and demonstrating that as the miscibility of the solvent in water decreases, the amount of water taken up into the implant decreases.
Figure 4B:
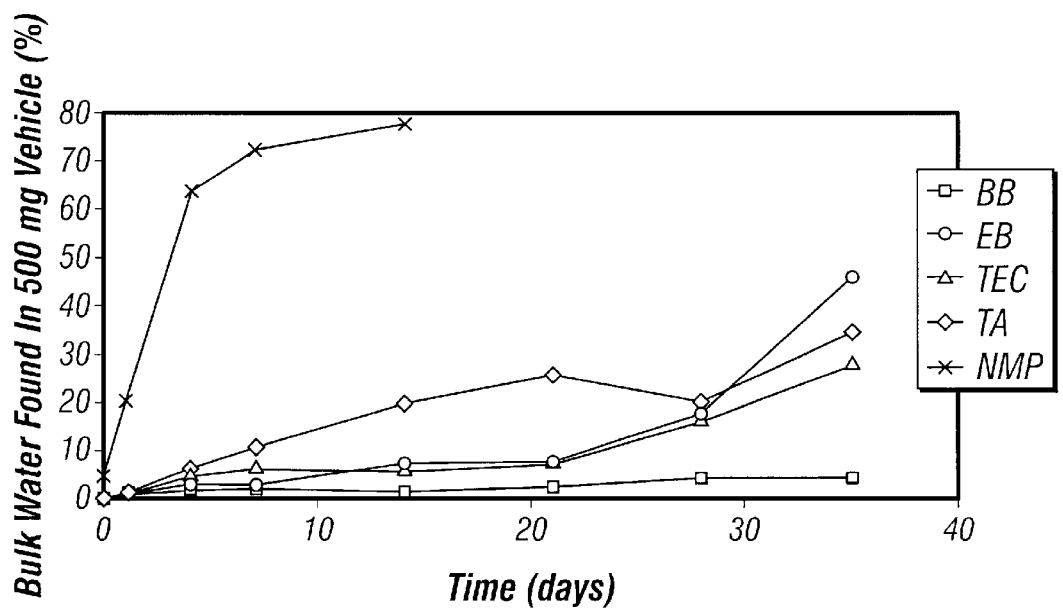

The importance of restriction of water uptake can be appreciated by reference to FIGS. 4A–4B illustrating bulk water uptake for various compositions as a function of time and Table 1 illustrating representative formulations for which burst indices have been determined.

Water uptake was determined for various polymer vehicles, i.e., 50% polymer-50% solvent compositions, in the absence of beneficial agent. As shown in FIG. 4A, water uptake by a gel vehicle formed with the more water miscible solvent N-methyl-2-pyrrolidone (NMP) is higher than that for any other solvent-polymer combination, by about a factor of four or more. Water uptake for the combination of 80% benzyl benzoate and 20% NMP by weight in the solvent portion of the vehicle is less than a third that of NMP alone. Implants with benzyl benzoate take up the least water, whether compared to the other solvents alone or as mixtures with benzyl benzoate. Additionally, it can be seen that the $^{80}/_{20}$ mixture of benzyl benzoate and triacetin takes up less than 10% water on a weight basis, and exhibits less water uptake than triacetin alone. FIG. 4B provides a comparison of various solvents alone and demonstrates again the advantages of the benzoic acid esters, particularly that of benzyl benzoate. A relative comparison of the water uptake for the various solvents and the burst indices reproduced in the foregoing Table 1 show a correlation between low water uptake values and low burst indices. Gel compositions of this invention may take up 25 % or less of their bulk weight in water within the first 7 days, 30% in the first 14 days and 40% in the first 21 days, as tested in the water migration assay described herein.

TABLE 1

| Solvent | Water Miscibility | Depot Gel[1] | Polymer[2] | Zinc acetate (mM) | Process[3] | Aninal No. | Burst Index |
|---|---|---|---|---|---|---|---|
| Benzyl Benzoate | insol. in water (Merck) | D | PLGA-502 | 0 | L | 7 | 4.2 |
|  |  |  |  |  |  | 8 | 2.4 |
|  |  | K | PLGA-502 | 0 | SD | 21 | 3.6 |
|  |  |  |  |  |  | 22 | 2.4 |
|  |  | E | PLGA-502 | 7.5 | L | 9 | 4.5 |
|  |  |  |  |  |  | 10 | 2.3 |
|  |  | L | PLGA-502 | 7.5 | SD | 23 | 2.6 |
|  |  |  |  |  |  | 24 | 2.1 |
|  |  | F | PLGA-502 | 15 | L | 11 | 1.5 |
|  |  |  |  |  |  | 12 | 2.0 |
|  |  | F | PLGA-502 | 15 | L | 25 | 2.2 |
|  |  |  |  |  |  | 26 | 0.64 |
| Triacetin | 7% sol. in water (Merck) | A | PLGA-502 | 0 | L | 1 | 8.5 |
|  |  |  |  |  |  | 2 | 13 |
|  |  | I | PLGA-502 | 0 | SD | 17 | 12 |
|  |  |  |  |  |  | 18 | 10 |
|  |  | B | PLGA-502 | 7.5 | L | 3 | 4.1 |
|  |  |  |  |  |  | 4 | 2.1 |
|  |  | J | PLGA-502 | 7.5 | SD | 19 | 6.3 |
|  |  |  |  |  |  | 20 | 3.5 |
|  |  | C | PLGA-502 | 15 | L | 5 | 4.8 |
|  |  |  |  |  |  | 6 | 3.5 |
| NMP | misc. with water (Merck) | G | PLGA-502 | 0 | L | 13 | 13 |
|  |  |  |  |  |  | 14 | 14 |
|  |  | H | PLGA-502 | 15 | L | 15 | 6.1 |
|  |  |  |  |  |  | 16 | 5.5 |

[1]All depot gels contained 10% hGH
[2]For all depot gels, hGH was loaded into (50/50) solvent/polymer vehicles
[3]L = Lyophilized;
SD = Spray-dried In addition to the control of water uptake and associated initial burst by choice of solvent, agents that modulate the water solubility of the beneficial agent can also be utilized in conjunction with the preferred solvents to control burst of beneficial agent from the implant. Burst indices and percent of beneficial agent released in the first twenty-four hours after implantation may be reduced by one-third to two-thirds or more by the use of solubility modulators associated with the beneficial agent. Such modulators are typically coatings, substances that form complexes or otherwise associate with or stabilize the beneficial agent such as metallic ions, other stabilizing agents, waxes, lipids, oils, non-polar emulsions, and the like. Use of such solubility modulators may permit the use of more highly water soluble solvents or mixtures and achieve burst indices of 8 or less for systemic applications, or with respect to local applications, release of beneficial agent in the first 24 hours after implantation of not greater than 20% of the beneficial agent administered. Preferably that release will be not greater than 15% and more preferably not greater than 10%.

Limited water uptake by the compositions of this invention can often provide the opportunity to prepare compositions without solubility modulators when in other compositions such modulators would be necessary. For example with reference to Table 1, suitable burst indices are obtained for a composition of PLGA, benzyl benzoate and human growth hormone without the presence of Zn ion. Similar results may be obtained with other beneficial agents, such as the interferons, including interferon alpha-2a, interferon alpha-2b and consensus interferon.

In instances where the choice of solvent and polymer result in compositions severely restricting water uptake by themselves, it may be desirable to add osmotic agents or other agents and hydroattractants that facilitate water uptake to desired levels. Such agents may be, for example, sugars and the like, and are well known in the art.

Limited water uptake by the solvent-polymer compositions of the present invention results in the implant compositions being formed without the finger-like pores in the surface of implants formed using prior art processes. Typically, a composition of the present invention takes the form of a substantially, homogeneous, sponge-like gel, with the pores in the interior of the implant being much the same as the pores on the surface of the implant. Compositions of the present invention retain their gel-like consistency over a longer period than do prior art devices and permit beneficial agent to be delivered over a prolonged period. This is possible since the implants of the present invention generally have a glass transition temperature, $T_g$, of less than body temperature of the subject, e.g. 37° C. for humans. Because of the immiscibility of the solvents that are useful in this invention with water, water uptake by the implant is restricted and the pores that do form tend to resemble a closed cell structure without significant numbers of larger pores or pores extending from the surface into the interior of the implant being open at the surface of the implant. Furthermore, the surface pores offer only a limited opportunity for water from body fluids to enter the implant immediately after implantation, thus controlling the burst effect. Since the compositions often will be highly viscous prior to implantation, when the composition is intended for implantation by injection, the viscosity optionally may be modified by the use of viscosity-reducing, miscible solvents or the use of emulsifiers, or by heating to obtain a gel composition having a viscosity or shear resistance low enough to permit passage of the gel composition through a needle.

The limit on the amount of beneficial agent released in the first 24 hours that is either desired or required will depend on circumstances such as the overall duration of the delivery period, the therapeutic window for the beneficial agent, potential adverse consequences due to overdosing, cost of beneficial agent, and the type of effect desired, e.g., systemic or local. Preferably, 20% or less of the beneficial agent will be released in the first 24 hours after implantation, where the percentage is based on the total amount of beneficial agent to be delivered over the duration of the delivery period. Typically, higher percentages of release in the first 24 hours can be tolerated if the duration of the delivery period is relatively short, e.g., less than 7–14 days, or if the beneficial agent has a wide therapeutic window with little likelihood of side effects, or if the beneficial agent acts locally.

Depending on the particular solvent or solvent mixture selected, the polymer and beneficial agent, and optionally solubility modulators of the beneficial agent, the compositions of the present invention intended for systemic delivery may provide a gel composition having a burst index of 8 or less, preferably 6 or less, more preferably 4 or less and most preferably 2 or less. Compositions of PLGA with solvents having a miscibility in water of less than 7% by weight, optionally combined with the other solvents, providing implants intended for systemic delivery of beneficial agent having a burst index of 10 or less, preferably 7 or less, more preferably 5 or less and most preferably 3 or less, are particularly advantageous. The use of solvent mixtures as discussed herein can be particularly advantageous as a means of providing sufficient plasticizing of the polymer to obtain viscous gel formation and at the same time meet the desired burst indices and percentage release objectives of the compositions of the invention.

Compositions intended for local delivery of beneficial agent are formed in the same manner as those intended for systemic use. However, because local delivery of beneficial agent to a subject will not result in detectable plasma levels of beneficial agent, such systems have to be characterized by a percentage of beneficial agent released in a predetermined initial period, rather than a burst index as defined herein. Most typically, that period will be the first 24 hours after implantation and the percentage will be equal to the amount by weight of the beneficial agent released in the period (e.g. 24 hours) divided by the amount by weight of the beneficial agent intended to be delivered in the duration of the delivery period; multiplied by the number 100. Compositions of the present invention will have initial bursts of 20% or less, preferably 15% or less, most preferably 10% or less, for most applications. Especially preferred are implant systems having initial bursts of 5% or less.

In many instances, it may be desirable to reduce the initial burst of beneficial agent during local administration to prevent adverse effects. For example, implants of the invention containing chemotherapeutic agents are suitable for direct injection into tumors. However, many chemotherapeutic agents may exhibit toxic side effects when administered systemically. Consequently, local administration into the tumor may be the treatment method of choice. It is necessary, however, to avoid administration of a large burst of the chemotherapeutic agent if it is possible that such agent would enter the vascular or lymphatic systems where it may exhibit side affects. Accordingly, in such instances the implantable systems of the present invention having limited burst as described herein are advantageous.

The solvent or solvent mixture is typically present in an amount of from about 95 to about 20% by weight and is preferably present in an amount of from about 70 to about 30% by weight and often 60–40% by weight of the viscous gel, i.e., the combined amounts of the polymer and the solvent. The viscous gel formed by mixing the polymer and the solvent typically exhibits a viscosity of from about 1,000 to about 200,000 poise, preferably from about 5,000 to about 50,000 poise measured at a 1.0 sec$^{-1}$ shear rate and 25° C. using a Haake Rheometer at about 1–2 days after mixing is completed. Mixing the polymer with the solvent can be achieved with conventional low shear equipment such as a Ross double planetary mixer for from about 10 minutes to about 1 hour, although shorter and longer periods may be chosen by one skilled in the art depending on the particular physical characteristics of the composition being prepared. Since it is often desirable to administer the implant as an injectable composition, a countervailing consideration when forming implants that are viscous gels is that the polymer/solvent/beneficial agent composition have sufficiently low viscosity in order to permit it to be forced through a small diameter, e.g., 18–20 gauge needle. If necessary, adjustment of viscosity of the gel for injection can be accomplished with emulsifying agents as described herein. Yet, such compositions should have adequate dimensional stability so as to remain localized and be able to be removed if necessary. The particular gel or gel-like compositions of the present invention satisfy such requirements.

If the polymer composition is to be administered as an injectable gel, the level of polymer dissolution will need to be balanced with the resulting gel viscosity, to permit a reasonable force to dispense the viscous gel from a needle, and the potential burst effect. Highly viscous gels enable the beneficial agent to be delivered without exhibiting a significant burst effect, but may make it difficult to dispense the gel through a needle. In those instances, an emulsifying agent may optionally be added to the composition. Also, since the viscosity may generally be lowered as the temperature of the composition increases, it may be advantageous in certain applications to reduce the viscosity of the gel by heating to provide a more readily injectable composition.

For instance, as shown in FIG. 1, a gel prepared from 40% by weight of a 50:50 lactic acid:glycolic polymer and 60% by weight of triacetin required about 40 psig to dispense the gel through a standard 20 gauge needle at 2 cc/min while a gel prepared from the same amount of polymer with 60% by weight of N-methyl-2-pyrrolidone required only about 8 psig. FIG. 1 further shows that when the emulsifying agent (in this case 33% by weight of a 10% ethanol solution) is added to the viscous gel according to the invention, the dispense force needed is only about 2 psig. The shear thinning characteristics of the depot gel compositions of the present invention allow them to be readily injected into an animal including humans using standard gauge needles without requiring undue dispensing pressure.

When the emulsifying agent is mixed with the viscous gel formed from the polymer and the solvent using conventional static or mechanical mixing devices, such as an orifice mixer, the emulsifying agent forms a separate phase composed of dispersed droplets of microscopic size that typically have an average diameter of less than about 100 microns. The continuous phase is formed of the polymer and the solvent. The particles of the beneficial agent may be dissolved or dispersed in either the continuous phase or the droplet phase. In the resulting thixotropic composition, the droplets of emulsifying agent elongate in the direction of shear and substantially decrease the viscosity of the viscous gel formed from the polymer and the solvent. For instance, with a viscous gel having a viscosity of from about 5,000 to about 50,000 poise measured at 1.0 sec$^{-1}$ at 25° C., one can obtain a reduction in viscosity to less than 100 poise when emulsified with a 10% ethanol/water solution at 25° C. as determined by Haake Rheometer.

When used, the emulsifying agent typically is present in an amount ranging from about 5 to about 80%, preferably from about 20 to about 60% and often 30 to 50% by weight based on the amount of the injectable depot gel composition, that is the combined amounts of polymer, solvent, emulsifying agent and beneficial agent. Emulsifying agents include, for example, solvents that are not fully miscible with the polymer solvent or solvent mixture. Illustrative emulsifying agents are water, alcohols, polyols, esters, carboxylic acids, ketones, aldehydes and mixtures thereof. Preferred emulsifying agents are alcohols, propylene glycol, ethylene glycol, glycerol, water, and solutions and mixtures thereof. Especially preferred are water, ethanol, and isopropyl alcohol and solutions and mixtures thereof. The type of emulsifying agent affects the size of the dispersed droplets. For instance, ethanol will provide droplets that have average diameters that can be on the order of ten times larger than the droplets obtained with an isotonic saline solution containing 0.9% by weight of sodium chloride at 21° C.

Figure 3:
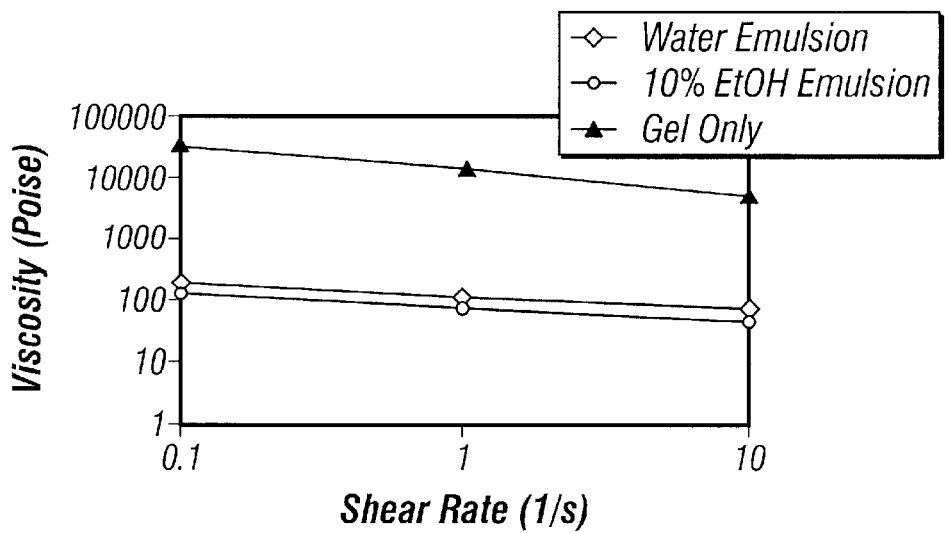
FIG. 3 is a graph illustrating the viscosity profiles of emulsions at different shear rates of water alone and of an aqueous mixture of ethanol, and of the viscous gel without emulsifying agent.

FIG. 3 shows the viscosities at different shear rates using water alone and an aqueous mixture containing 10% by volume of ethanol at a weight ratio of 2:1 (gel:emulsifying agent) using a viscous gel formed from 50% by weight of a 50:50 lactic acid:glycolic acid copolymer and 50% by weight of triacetin compared to the viscosities of the viscous gel without emulsifying agent.

It is to be understood that the emulsifying agent does not constitute a mere diluent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the solvent and emulsifying agent so that once injected into place, the emulsifying agent has little impact on the release properties of the original system.

Since the implant systems of the present invention preferably are formed as viscous gels, the means of administration of the implants is not limited to injection, although that mode of delivery may often be preferred. Where the implant will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

The beneficial agent can be any physiologically or pharmacologically active substance or substances optionally in combination with pharmaceutically acceptable carriers and additional ingredients such as antioxidants, stabilizing agents, permeation enhancers, etc. that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, antiinflammatory corticosteroids, ocular drugs and synthetic analogs of these species.

Examples of drugs which may be delivered by the composition of the present invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, bovine growth hormone and porcine growth hormone, fertility inhibitors such as the prostaglandins, fertility promoters, growth factors such as insulin-like growth factor, coagulation factors, human pancreas hormone releasing factor, analogs and derivatives of these compounds, and pharmaceutically acceptable salts of these compounds, or their analogs or derivatives.

The present invention also finds application with chemotherapeutic agents for the local application of such agents to avoid or minimize systemic side effects. Gels of the present invention containing chemotherapeutic agents may be injected directly into the tumor tissue for sustained delivery of the chemotherapeutic agent over time. In some cases, particularly after resection of the tumor, the gel may be implanted directly into the resulting cavity or may be applied to the remaining tissue as a coating. In cases in which the gel is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as for example cisplatin and carboplatin and the water soluble derivatives of paclitaxel. Those characteristics of the invention that minimize the burst effect are particularly advantageous in the administration of water soluble beneficial agents of all kinds, but particularly those compounds that are clinically useful and effective but may have adverse side effects.

To the extent not mentioned above, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microencapsulate or process into microspheres can be incorporated into the compositions of the present invention without the level of degradation caused by exposure to high temperatures and denaturing solvents often present in other processing techniques.

The beneficial agent is preferably incorporated into the viscous gel formed from the polymer and the solvent in the form of particles typically having an average particle size of from about 0.1 to about 100 microns, preferably from about 1 to about 25 microns and often from 2 to 10 microns. For instance, particles having an average particle size of about 5 microns have been produced by spray drying or freeze drying an aqueous mixture containing 50% sucrose and 50% chicken lysozyme (on a dry weight basis) and mixtures of 10–20% hGH and 15–30 mM zinc acetate. Such particles have been used in certain of the examples illustrated in the figures. Conventional lyophilization processes can also be utilized to form particles of beneficial agents of varying sizes using appropriate freezing and drying cycles.

To form a suspension or dispersion of particles of the beneficial agent in the viscous gel formed from the polymer and the solvent, any conventional low shear device can be used such as a Ross double planetary mixer at ambient conditions. In this manner, efficient distribution of the beneficial agent can be achieved substantially without degrading the beneficial agent.

The beneficial agent is typically dissolved or dispersed in the composition in an amount of from about 1 to about 50% by weight, preferably in an amount of from about 5 to about 30% and often 10 to 20% by weight of the combined amounts of the polymer, solvent and beneficial agent. Depending on the amount of beneficial agent present in the composition, one can obtain different release profiles and burst indices. More specifically, for a given polymer and solvent, by adjusting the amounts of these components and the amount of the beneficial agent, one can obtain a release profile that depends more on the degradation of the polymer than the diffusion of the beneficial agent from the composition or vice versa. In this respect, at lower beneficial agent loading rates, one generally obtains a release profile reflecting degradation of the polymer wherein the release rate increases with time. At higher loading rates, one generally obtains a release profile caused by diffusion of the beneficial agent wherein the release rate decreases with time. At intermediate loading rates, one obtains combined release profiles so that if desired, a substantially constant release rate can be attained. In order to minimize burst, loading of beneficial agent on the order of 30% or less by weight of the overall gel composition, i.e., polymer, solvent and beneficial agent, is preferred, and loading of 20% or less is more preferred.

Release rates and loading of beneficial agent will be adjusted to provide for therapeutically-effective delivery of the beneficial agent over the intended sustained delivery period. Preferably, the beneficial agent will be present in the polymer gel at concentrations that are above the saturation concentration of beneficial agent in water to provide a drug reservoir from which the beneficial agent is dispensed. While the release rate of beneficial agent depends on the particular circumstances, such as the beneficial agent to be administered, release rates on the order of from about 0.1 to about 100 micrograms/day, preferably from about 1 to about 10 micrograms per day, for periods of from about 7 to about 90 days can be obtained. Greater amounts may be delivered if delivery is to occur over shorter periods. Generally, higher release rate is possible if a greater burst can be tolerated. In instances where the gel composition is surgically implanted, or used as a "leave behind" depot when surgery to treat the disease state or another condition is concurrently conducted, it is possible to provide higher doses that would normally be administered if the implant was injected. Further, the dose of beneficial agent may be controlled by adjusting the volume of the gel implanted or the injectable gel injected. As can be seen from FIG. 2 with respect to lysozyme, with more highly viscous systems, one can avoid a burst effect and deliver on the order of 1% by weight of the beneficial agent in the composition during the first day.

Figure 5A:
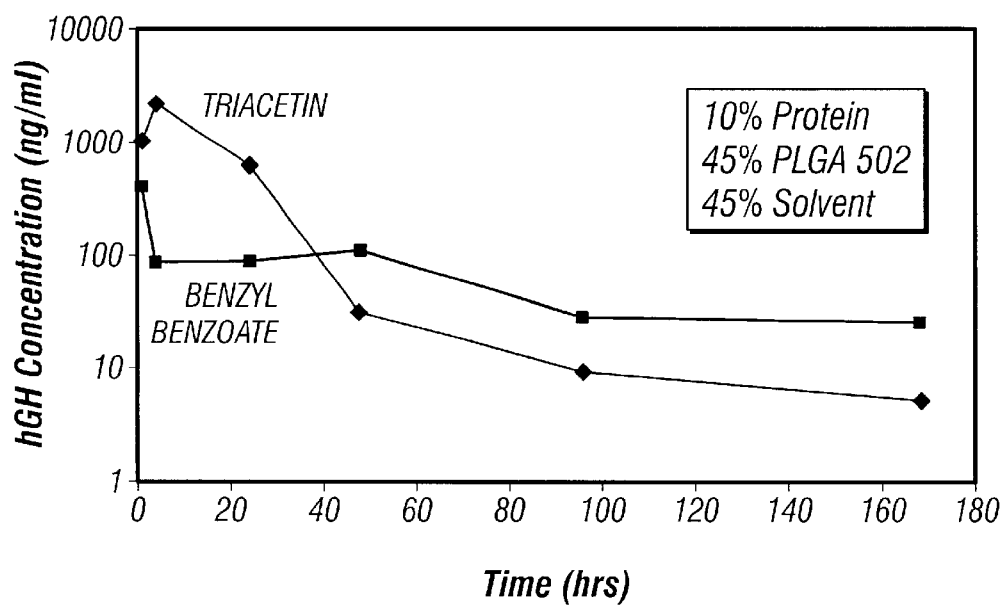
FIGS. 5A and 5B are graphs of in vivo release rate profiles of non-stabilized and zinc-stabilized human growth hormone from gels formed from PLGA and the solvents triacetin and benzyl benzoate, respectively.
Figure 5B:
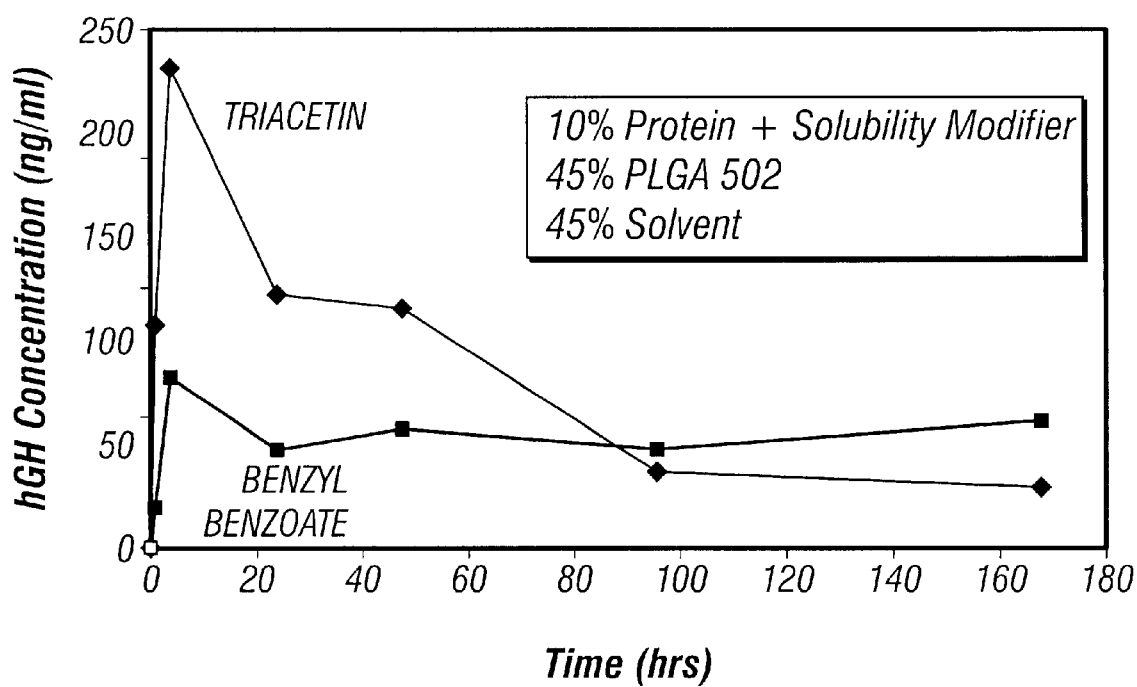

FIGS. 5A and 5B illustrate representative release profiles of human growth hormone ("hGH") obtained in rats from preferred compositions of this invention. The benefits of benzyl benzoate are apparent in that comparison. The hGH-benzyl benzoate implant shows a lower burst and a nearly zero order sustained release of hGH over the release period for both the case wherein the hGH is not stabilized (FIG. 5A) and the case in which hGH is stabilized with zinc ions (FIG. 5B).

Other components may be present in the gel composition, to the extent they are desired or provide useful properties to the composition, such as polyethylene glycol, hydroscopic agents, stabilizing agents, pore forming agents, and others. When the composition includes a peptide or a protein that is soluble in or unstable in an aqueous environment, it may be highly desirable to include a solubility modulator, that may, for example, be a stabilizing agent, in the composition. Various modulating agents are described in U.S. Pat. Nos. 5,654,010 and 5,656,297 which are incorporated herein by reference. In the case of hGH, for example, it is preferable to include an amount of a salt of a divalent metal, preferably zinc.

Examples of such modulators and stabilizing agents, which may form complexes with the beneficial agent or associate to provide the stabilizing or modulated release effect, include metal cations, preferably divalent, present in the composition as magnesium carbonate, zinc carbonate, calcium carbonate, magnesium acetate, magnesium sulfate, zinc acetate, zinc sulfate, zinc chloride, magnesium chloride, magnesium oxide, magnesium hydroxide, other antacids, and the like. The amounts of such agents used will depend on the nature of the complex formed, if any, or the nature of the association between the beneficial agent and the agent. Molar ratios of solubility modulator or stabilizing agent to beneficial agent of about 100:1 to 1:1, preferably 10:1 to 1:1, typically can be utilized.

Pore forming agents include, biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxmethylcellulose, hydroxypropylcellulose, and the like) can conveniently be used as pore formers. Such materials may be present in amounts varying from about 0.1% to about 100% of the weight of the polymer, but will typically be less than 50% and more typically less than 10–20% of the weight of polymer.

Compositions of this invention without beneficial agent are useful for wound healing, bone repair and other structural support purposes.

To further understand the various aspects of the present invention, the results set forth in the previously described Figures were obtained in accordance with the following examples.

EXAMPLE 1

Lysozyme particles were made by spray drying 50% sucrose and 50% chicken lysozyme (on a dry weight basis).

A viscous gel material was prepared by heating 60% by weight of triacetin with 40% by weight of a 50:50 lactic acid:glycolic acid copolymer to 37° C. overnight. The viscous gel was allowed to cool to room temperature. The lysozyme particles were added to the viscous gel in a ratio of 20:80 lysozyme particles:gel (by weight). The combination was mixed for 5 minutes. Immediately prior to use, a 10% ethanol, 90% isotonic saline solution was added as the emulsifying agent. The emulsifying agent comprised ⅓ of the total injectable depot gel composition. The prepared compositions were suitable for injection.

Figure 2:
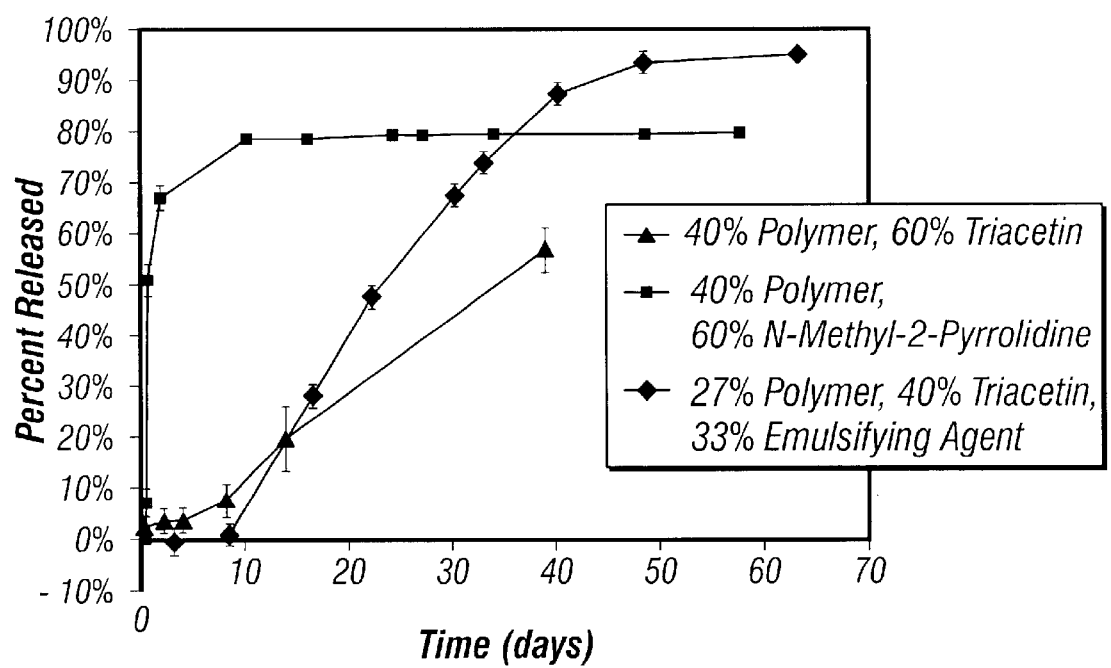
FIG. 2 is a graph illustrating the in vitro release profiles of lysozyme from three different compositions in days.

FIG. 2 shows the in vitro release rates obtained from the compositions described with regard to FIG. 1. The gel prepared from 40% by weight of a 50:50 lactic acid:glycolic polymer and 60% by weight triacetin is thick and thus difficult to inject but shows little burst (less than 2% of the beneficial agent is delivered in the first eight days). The gel prepared from 40% by weight of a 50:50 lactic acid:glycolic polymer and 60% by weight n-methyl-2-pyrrolidone is thin and injectable but shows a large burst (greater than 70% of the beneficial agent is delivered in the first eight days). The gel prepared from 27% by weight of a 50:50 lactic acid:glycolic polymer, 40% by weight triacetin and 33% by weight of a 10% ethanol, 90% isotonic saline solution is thin and injectable and shows little burst (less than 10% of the beneficial agent is delivered in the first eight days). In each case, lysozyme is the beneficial agent and comprises 20% by weight of the combined beneficial agent, polymer and solvent formulation.

EXAMPLE 2 hGH Particle Preparation

Human growth hormone (hGH) particles (optionally containing zinc acetate) were prepared as follows:

hGH solution (5 mg/ml) solution in water (BresaGen Corporation, Adelaide, Australia) was concentrated to 10 mg/mL using a Concentration/Dialysis Selector diafiltering apparatus. The diafiltered hGH solution was then washed with 5 times volume of tris or phosphate buffer solution (pH 7.6). Particles of hGH were then formed by spray drying or lyophilization using conventional techniques. Phosphate buffer solutions (5 or 50 mM) containing hGH (5 mg/mL) and various levels of zinc acetate (0 to 30 mM) were spray-dried using a Yamato Mini Spraydryer set at the following parameters:

| Spray Dryer Parameter | Setting |
| --- | --- |
| Atomizing Air | 2 psi |
| Inlet Temperature | 120° C. |
| Aspirator Dial | 7.5 |
| Solution Pump | 2–4 |
| Main Air Valve | 40–45 psi | hGH particles having a size range between 2–100 microns were obtained. Lyophilized particles were prepared from tris buffer solutions (5 or 50 mM: pH 7.6) containing hGH (5 mg/mL) and various levels of zinc acetate (0 to 30 mM) using a Durastop μP Lyophilizer in accordance with the following freezing and drying cycles:

| | |
| --- | --- |
| Freezing Cycle | Ramp down at 2.5 C./min to −30 C. and hold for 30 minutes |
| | Ramp down at 2.5 C./min from −30 C. to −50 C. and hold for 60 minutes |
| Drying Cycle | Ramp up at 0.5 C./min to 10 C. and hold for 960 min |
| | Ramp up at 0.5 C./min to 20 C. and hold for 480 min |
| | Ramp up at 0.5 C./min to 25 C. and hold for 300 min |
| | Ramp up at 0.5 C./min to 30 C. and hold for 300 min |
| | Ramp down at 0.5 C./min to 5 C. and hold for 5000 min | hGH particles having a size range between 2–100 microns were obtained.

hGH Zinc Complexed Solution Preparation

Zinc acetate solutions were prepared with tris buffer and phosphate buffer. Desired molar volumes of trizma hydrochloride and trizma base were prepared separately (5 or 50 mM). The pH of trizma base solution was measured, and the corresponding trizma hydrochloride solution was added to adjust the pH of the trizma base solution, resulting with a final pH of 7.6. The desired molar volume of zinc acetate was added to the buffer solution. Desired molar volumes of sodium phosphate monobasic and sodium phosphate diabasic were prepared separately (5 or 50 mM). Sodium azide (0.2% w/w) was added to each phosphate solution. The pH of the dibasic solution was measured, and the corresponding monobasic solution was added to adjust the pH of the dibasic solution, resulting with a final pH of 7.6. The desired molar volume of zinc acetate was added to the buffer solution. Tris or phosphate buffer containing zinc acetate was added to the diafiltered hGH solution to achieve the final desired zinc acetate molar volume (between 5 and 30 mM). The final hGH concentration was 5 mg/mL.

Gel Vehicle Preparation

A glass vessel was tared on a Mettler PJ3000 top loader balance. Poly (D,L-lactide-co-glycolide) 50:50 RESOMER® RG502 (PLGA-502) was weighed into the glass vessel. The glass vessel containing PLGA-502 was tared and the corresponding solvent was added. Amounts expressed as percentages for various polymer/solvent combinations are set forth in Table 2 below. The polymer/solvent mixture was manually stirred with a stainless steel square-tip spatula, resulting in a sticky amber paste-like substance containing white polymer particles. The vessel containing the polymer/solvent mixture was sealed and placed in a temperature controlled incubator equilibrated to 39° C. The polymer/solvent mixture was removed from the incubator when it appeared to be a clear amber homogeneous gel. Incubation time intervals ranged from 1 to 4 days, depending on solvent and polymer type and solvent and polymer ratios. Additional depot gel vehicles are prepared with the following polymers: Poly (D,L-lactide-co-glycolide) 50:50 RESOMER® L104, PLGA-L104, code no. 33007, Poly (D,L-lactide-co-glycolide) 50:50 RESOMER® RG206, PLGA-206, code no. 8815, Poly (D,L-lactide-co-glycolide) 50:50 RESOMER® RG502, PLGA-502, code 0000366, Poly (D,L-lactide-co-glycolide) 50:50 RESOMER® RG502H, PLGA-502H, code no. 260187, Poly (D,L-lactide-co-glycolide) 50:50 RESOMER® RG503, PLGA-503, code no. 0080765, Poly (D,L-lactide-co-glycolide) 50:50 RESOMER® RG506, PLGA-506, code no. 95051, Poly (D,L-lactide-co-glycolide) 50:50 RESOMER® RG755, PLGA-755, code no. 95037, (Boehringer Ingelheim Chemicals, Inc., Petersburg, Va.), and the following solvents or mixtures: glyceryl triacetate (Eastman Chemical Co., Kingsport, Tenn.), benzyl benzoate ("BB"), ethyl benzoate ("EB"), methyl benzoate ("MB"), triacetin ("TA"), and triethyl citrate ("TC") (Aldrich Chemical Co., St Louis, Mo.). When solvent combinations were used, for example 20% triacetin and 80% benzyl benzoate, the solvent mixture was directly added to the pre-weighed dry polymer. Typical polymer molecular weights were in the range of 14,400–39,700 ($M_w$) [6,400–12,200 ($M_n$)]. Representative gel vehicles are described in Table 2 below.

TABLE 2

Gel Vehicles

| Solvent/ Polymer | Solvent | Polymer | Amount Solvent | Amount Polymer | Gel Weight | Ratio |
|---|---|---|---|---|---|---|
| 50/50 | BB | PLGA-502 | 5 g | 5 g | 10 g | 1.0 |
| 50/50 | TA/BB Mixture | PLGA-502 | 5 g | 5 g | 10 g | 1.0 |
| 60/40 | TA/BB Mixture | PLGA-502 | 6 g | 4 g | 10 g | 1.5 |
| 70/30 | TA/BB Mixture | PLGA-502 | 7 g | 3 g | 10 g | 2.3 |
| 80/20 | TA/BB Mixture | PLGA-502 | 8 g | 2 g | 10 g | 4.0 |
| 50/50 | EB | PLGA-502 | 5 g | 5 g | 10 g | 1.0 |
| 50/50 | TA/EB Mixture | PLGA-502 | 5 g | 5 g | 10 g | 1.0 |
| 50/50 | BB | PLGA-502 | 25 g | 25 g | 50 g | 1.0 |
| 55/45 | BB | PLGA-502 | 27.5 g | 22.5 g | 50 g | 1.2 |
| 50/50 | BB | PLGA-502 | 50 g | 50 g | 100 g | 1.0 |
| 50/50 | TA/BB Mixture | PLGA-502 | 50 g | 50 g | 100 g | 1.0 |
| 50/50 | BB | PLGA-502H | 5 g | 5 g | 10 g | 1.0 |
| 50/50 | BB | PLGA-503 | 50 g | 50 g | 100 g | 1.0 |

Drug Loading

Spray-dried or lyophilized hGH particles (10–20% w/w), with and without zinc acetate, prepared as above were added to a specified clear amber depot gel vehicle and blended manually until the dry powder was wetted completely. Then, the milky light yellow particle/gel mixture was thoroughly blended by conventional mixing using a Caframo mechanical stirrer with an attached square-tip metal spatula. Resulting formulations are illustrated in Tables 3 and 4 below. "L" identifies lyophilized hGH particles and "SD" identifies spray dried hGH particles. Final homogenous gel formulations were transferred to 3, 10 or 30 cc disposable syringes for storage or dispensing.

TABLE 3

In Vivo hGH

| | Polymer | | Solvent | | Drug Particle | | | |
|---|---|---|---|---|---|---|---|---|
| Formulation | Level | PLGA | Level | Type | Level | Process | Zinc Level (mM) | Trizma Buffer (mM) |
| A | 45% | 502 | 45% | TA | 10% | L | 0 | 50 |
| B | 45% | 502 | 45% | TA | 10% | L | 7.5 | 50 |
| C | 45% | 502 | 45% | TA | 10% | L | 15 | 50 |
| D | 45% | 502 | 45% | BB | 10% | L | 0 | 50 |
| E | 45% | 502 | 45% | BB | 10% | L | 7.5 | 50 |
| F | 45% | 502 | 45% | BB | 10% | L | 15 | 50 |
| G | 45% | 502 | 45% | NMP | 10% | L | 0 | 50 |
| H | 45% | 502 | 45% | NMP | 10% | L | 15 | 50 |
| I | 45% | 502 | 45% | TA | 10% | SD | 0 | 50 |
| J | 45% | 502 | 45% | TA | 10% | SD | 7.5 | 50 |
| K | 45% | 502 | 45% | BB | 10% | SD | 0 | 50 |
| L | 45% | 502 | 45% | BB | 10% | SD | 7.5 | 50 |

TABLE 4

In Vivo hGH (zinc level in all cases was 15 mM)

| Formulation | Polymer | | Solvent | | Drug Particle | | Trizma Buffer (mM) |
|---|---|---|---|---|---|---|---|
| | Level | PLGA | Level | Type | Level | Process | |
| F | 45% | 502 | 45% | BB | 10% | L | 50 |
| N | 45% | 502 | 45% | 80% BB/20% TA | 10% | L | 5 |
| P | 45% | 502H | 45% | TA | 10% | L | 5 |
| Q | 45% | 502H | 45% | BB | 10% | L | 5 |
| R | 45% | 502 | 45% | EB | 10% | L | 5 |
| S | 45% | 502 | 45% | TC | 10% | L | 5 |
| T | 40% | 502 | 45% | BB | 20% | L | 5 |
| W | 45% | 502-2 | 45% | BB | 10% | L | 5 |
| X | 45% | 502 | 45% | TA | 10% | L | 5 |

EXAMPLE 3

Lysozyme In Vitro Studies

Lysozyme from chicken egg white (Sigma Chemical Co., St Louis, Mo.) in vitro release studies were used to test different vehicle formulations with the highly water soluble solvent NMP and the less soluble solvents triacetin and benzyl benzoate useful in the present invention. A depot gel formulation was dispensed from a 3 cc disposable syringe and weighed onto a Delrin™ cup platform or a 250 μ mesh 1 square inch polypropylene screen. Then, the cup or screen containing a depot gel formulation was immersed into a plastic vial containing 10 mL of receptor buffer. A snap-on lid was placed onto the plastic vial to prevent evaporation. The vial containing the depot gel formulation was immersed into a Haake shaking water bath equilibrated to 37° C. At each time point, forceps were used to transfer Delrin™ cup platforms or polypropylene screen platforms containing depot gel formulations to new plastic vials containing 10 mL of receptor buffer. Disposable transfer pipettes were used to transfer receptor samples to HPLC vials. The receptor buffer was phosphate buffered saline, PBS, adjusted to pH 7 containing sodium azide (0.2%). Receptor buffers contained tween-80 (0.1%) for most cases. Collection intervals were typically 2, 4, 8 hours, 1, 2, 3, 4, 7, 10 days, and 2, 3, 4, 5, 6, 7, 8 weeks. All receptor samples were analyzed for lysozyme concentration using a gradient elution Reverse-Phase High Performance Liquid Chromatography (RP-HPLC) assay with a refrigerated autosampler (4° C). Results indicated that the compositions of the present invention using benzyl benzoate and benzyl benzoate solvent mixtures exhibited substantially less burst of lysozyme than that exhibited by the gel compositions formed with NMP.

EXAMPLE 4

In Vitro Water Content Studies

The same procedure was used as described in Example 3 for in vitro drug release using the Delrin™ cup platform, except the entire cup platform containing the depot gel vehicle was removed, blotted dry, and placed in a dry plastic vial at specified time intervals. The receptor solution was sterile water and replaced at each time interval for the remaining samples. Initial and final depot gel vehicle weights were recorded to observe weight change. Water content was obtained from depot gel vehicles using a Karl Fischer Apparatus, Mitsubishi Moisture Meter CA-06 equipped with Vaporizer VA-06.

Results are illustrated in FIGS. 4A–4B for selected gels. Those results demonstrate that gel compositions of this invention take up substantially less water than gel compositions formed with NMP alone.

EXAMPLE 5 hGH In Vivo Studies

In vivo studies in rats were performed following an open protocol to determine serum levels of hGH upon systemic administration of hGH via the implant systems of this invention. Depot gel hGH formulations, spray-dried (SD) or lyophilized (L), were loaded into customized 0.5 cc disposable syringes. Disposable 16 gauge needles were attached to the syringes and were heated to 37° C. using a circulator bath. Depot gel hGH formulations were injected into rats and blood was drawn at specified time intervals. All serum samples were stored at 4° C. prior to analysis. Samples were analyzed for intact hGH content using a radio immuno assay (RIA). Representative results for triacetin and benzyl benzoate are illustrated in FIGS. 5A and 5B, and demonstrate the superior control of burst by the compositions of the present invention.

EXAMPLE 6

Implant systems of this invention are prepared in accordance with Example 2 with equivalent quantities of interferon alpha-2a and -2b, consensus interferon, methionine human growth hormone, des-phenylalanine human growth hormone, carboplatin and insulin-like growth factor. The amount of the viscous gel containing drug administered to rats in accordance with Example 5 is adjusted to take into account the relative biological activity of the separate agents. The implant systems are implanted in rats to provide systemic levels of active agent.

EXAMPLE 7

Implant systems containing carboplatin are prepared according to Example 6 and injected directly into solid tumors of tumor bearing rats. The implant systems are suitable for local delivery of carboplatin to tumors.

EXAMPLE 8

100 Mg implantable depots containing 0.5, 1.5 and 3 mg of interferon alpha-2b, stabilized with 0.5, 1 and 2 mg of sucrose, respectively, and the remainder being 50 mg benzyl benzoate and 45–49 mg of PLGA 502 as applicable (number average molecular weight of about 10,000) are prepared in accordance with Example 2 (without the addition of zinc). The implants exhibit limited burst and are suitable for implantation. The implant systems are implanted in rats to provide systemic levels of interferon alpha-2b.

In accordance with various aspects of the present invention, one or more significant advantages can be obtained. More specifically, implantable or injectable viscous gels containing beneficial agent for systemic and local administration are obtained that exhibit low or minimal burst effect when implanted. Furthermore, using simple processing steps, one can obtain a gel composition that can be surgically implanted in an animal or injected into place in an animal without surgery using a low dispensing force through standard needles. Once in place, the composition will substantially avoid a burst effect and provide the desired beneficial agent release profile. Furthermore, once the beneficial agent has been fully administered, there is no need to remove the composition since it is fully biodegradable. As a still further advantage, the present invention avoids the use of microparticle or microencapsulation techniques which can degrade certain beneficial agents, like peptide and nucleic acid-based drugs and which microparticles and microcapsules may be difficult to remove from the environment of use. Since the viscous gel is formed without the need for water, temperature extremes, or other solvents, suspended particles of beneficial agent remain dry and in their original configuration, which contributes to the stability of thereof. Further, since a mass is formed, the injectable depot gel composition may be retrieved from the environment of use if desired.

The above-described exemplary embodiments are intended to be illustrative in all respects, rather than restrictive, of the present Invention. Thus the present invention is capable of many variations in detailed implementation that can be derived from the description contained herein by a person skilled in the art. All such variations and modifications are considered to be within the scope and spirit of the present invention as defined by the following claims.

We claim:

1. A method of systemically administering a beneficial agent to a subject which comprises implanting a system comprising a polylactide polymer; an effective plasticizing amount of a solvent comprising a lower alkyl or aralkyl ester of benzoic acid to form a gel with the polymer; and a beneficial agent; wherein said beneficial agent is dissolved or dispersed substantially throughout the gel.

2. The method of claim 1 in which the gel includes one or more of the following: an emulsifying agent, a pore former, a solubility modulator for the beneficial agent and an osmotic agent.

3. The method of claim 1 wherein the solvent comprises a solvent having a miscibility in water of less than 7% by weight.

4. The method of claim 3 wherein the solvent is selected from the group consisting of benzyl benzoate and ethyl benzoate.

5. A method of administering a beneficial agent to a subject which comprises implanting a system comprising a beneficial agent dissolved or dispersed substantially throughout a gel formed of a polylactide polymer and a solvent having a solubility in water of 7% or less, wherein said solvent is a lower alkyl or aralkyl ester of benzoic acid, and a solubility modulator of the beneficial agent.

6. The method of claim 5 wherein the polymer is a lactic acid-based polymer.

7. The method of claim 1 wherein the beneficial agent is present in an amount of from 1 to 50% by weight of the combined amounts of the polymer, the solvent and the beneficial agent.

8. The method of claim 1 wherein the beneficial agent is cDNA, DNA, a protein, a peptide, and derivatives or fragments thereof, or a chemotherapeutic agent.

9. The method of claim 8 wherein the beneficial agent is human growth hormone, methionine-human growth hormone, des-phenylalanine human growth hormone, interferon alpha-2a, interferon alpha-2b, or consensus interferon.

10. The method of claim 1 wherein the system is non-rigid after implantation.

11. The method of claim 10 wherein the system maintains a glass transition temperature below 37° C. for at least 24 hours after implantation.

12. The method of claim 4 comprising a solubility modulator of the beneficial agent.

13. The method of claim 4 comprising a pore former.

14. The method of claim 4 comprising an emulsifying agent.

15. The method of claim 4 comprising an osmotic agent.

16. The method of claim 2 or claim 12 wherein the solubility modulator is selected from salts of divalent metals.

17. The method of claim 2 or claim 13 in which the pore former is water soluble.

18. The method of claim 17 wherein the pore former is selected from group consisting of water soluble sugars, salts, solvents and polymers.

19. The method of claim 2 or claim 14 in which the emulsifying agent is capable of forming a dispersed droplet phase in said gel.

20. The method of claim 19 in which the emulsifying agent is selected from the group consisting of alcohols, propylene glycol, ethylene glycol, glycerol, water and solutions and mixtures thereof.

21. The method of claim 20 wherein the emulsifying agent is selected from the group consisting of ethanol, isopropyl alcohol, water, solutions thereof, and mixtures thereof.

22. The method of claim 1 wherein the polylactide polymer is a copolymer of lactic acid and glycolic acid and the copolymer has a monomer ratio of lactic acid to glycolic acid in the range of about 100:0 to about 15:85.

23. The method of claim 22 wherein the copolymer has a number average molecular weight of from 1,000 to 120,000.

24. The method of claim 4 wherein the solvent comprises a component solvent miscible with the solvent.

25. The method of claim 24 wherein the component solvent is selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one, and mixtures thereof.

26. The method of claim 24 wherein the component solvent is selected from the group consisting of triacetin and N-methyl-2-pyrrolidone, and mixtures thereof.

27. The method of claim 24 wherein the component solvent is triacetin.

28. The method of claim 4 wherein the beneficial agent is present in an amount of from 1 to 50% by weight of the combined amounts of the polymer, the solvent and the beneficial agent.

29. The method of claim 4 wherein the beneficial agent is cDNA, DNA, a protein, a peptide, and derivatives or fragments thereof, or a chemotherapeutic agent.

30. The method of claim 4 wherein the beneficial agent is a human growth hormone, methionine-human growth hormone, des-pheylalanine human growth hormone, interferon alpha-2a, or consessus interferon.

31. A method of systemically administering a beneficial agent to a subject which comprises implanting a system comprising a poly(lactide-co-glycolide) copolymer; an effective plasticizing amount of a solvent comprising a lower alkyl or aralkyl ester of benzoic acid to form a gel with the polymer; and a beneficial agent; said beneficial agent dissolved or dispersed substantially throughout the gel.

32. The method of claim 31 wherein the solvent has a miscibility in water by weight of less than 7%.

33. The method of claim 31 wherein the solvent is benzyl benzoate.

34. The method of claim 31 comprising a solubility modulator of the beneficial agent.

35. The method of claim 31 comprising a pore former.

36. The method of claim 31 comprising an emulsifying agent.

37. The method of claim 31 comprising an osmotic agent.

38. The method of claim 34 wherein the solubility modulator is selected from salts of divalent metals.

39. The method of claim 35 in which the pore former is water soluble.

40. The method of claim 35 wherein the pore former is selected from group consisting of water soluble sugars, salts, solvents and polymers.

41. The method of claim 36 in which the emulsifying agent is capable of forming a dispersed droplet phase in said gel.

42. The method of claim 36 in which the emulsifying agent is selected from the group consisting of alcohols, propylene glycol, ethylene glycol, glycerol, water and solutions and mixtures thereof.

43. The method of claim 36 wherein the emulsifying agent is selected from the group consisting of ethanol, isopropyl alcohol, water, solutions thereof, and mixtures thereof.

44. The method of claim 31 wherein the copolymer has a monomer ratio of lactic acid to glycolic acid in the range of 100:0 to about 15:85.

45. The method of claim 31 wherein the copolymer has a number average molecular weight of from 1,000 to 120,000.

46. The method of claim 31 wherein the solvent comprises a component solvent miscible with the solvent.

47. The method of claim 46 wherein the component solvent is selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one, and mixtures thereof.

48. The method of claim 46 wherein the component solvent is selected from the group consisting of triacetin and N-methyl-2-pyrrolidone, and mixtures thereof.

49. The method of claim 46 wherein the component solvent is triacetin.

50. The method of claim 31 wherein the beneficial agent is present in an amount of from 1 to 50% by weight of the combined amounts of the polymer, the solvent, and the beneficial agent.

51. The method of claim 31 wherein the beneficial agent is cDNA, DNA, a protein, a peptide, and derivatives or fragments thereof, or a chemotherapeutic agent.

52. The method of claim 31 wherein the beneficial agent is human growth hormone, methionine-human growth hormone, des-phenylalanine human growth hormone, interferon alpha-2a, interferon alpha-2b, or consensus interferon.

53. The method of claim 31 wherein the solvent is ethyl benzoate.

54. The method of claim 31 wherein the system is non-rigid after implantation.

55. The method of claim 54 wherein the system maintains a glass transition temperature below 37° C. for at least 24 hours after implantation.

56. A method of systemically administering a beneficial agent to a subject which comprises implanting a system comprising a beneficial agent dissolved or dispersed substantially throughout a gel formed of a polylactide polymer; an amount of a solvent comprising a lower alkyl or aralkyl ester of benzoic acid effective to form a viscous gel, having a viscosity of from about 1,000 poise to about 200,000 poise, with the polymer; and a beneficial agent.

57. A method of systemically administering a beneficial agent to a subject which comprises implanting a system comprising a beneficial agent dissolved or dispersed substantially throughout a gel formed of a poly(lactide-co-glycolide) copolymer; an amount of a solvent comprising a lower alkyl or aralkyl ester of benzoic acid effective to form a viscous gel, having a viscosity of from about 1,000 poise to about 200,000 poise, with the polymer; and a beneficial agent.

58. The method of claim 56 or claim 57 wherein the solvent has a miscibility in water by weight of less than 7%.

59. The method of claim 56 or claim 57 wherein the solvent is benzyl benzoate.

60. The method of claim 56 or claim 57 comprising a solubility modulator of the beneficial agent.

61. The method of claim 56 or claim 57 comprising a pore former.

62. The method of claim 56 or claim 57 comprising an emulsifying agent.

63. The method of claim 56 or claim 57 comprising an osmotic agent.

64. The method of claim 60 wherein the solubility modulator is selected from salts of divalent metals.

65. The method of claim 61 in which the pore former is water soluble.

66. The method of claim 61 wherein the pore former is selected from group consisting of water soluble sugars, salts, solvents and polymers.

67. The method of claim 62 in which the emulsifying agent is capable of forming a dispersed droplet phase in said gel.

68. The method of claim 62 in which the emulsifying agent is selected from the group consisting of alcohols, propylene glycol, ethylene glycol, glycerol, water and solutions and mixtures thereof.

69. The method of claim 62 wherein the emulsifying agent is selected from the group consisting of ethanol, isopropyl alcohol, water, solutions thereof, and mixtures thereof.

70. The method of claim 56 or claim 57 wherein the copolymer has a monomer ratio of lactic acid to glycolic acid in the range of 100:0 to about 15:85.

71. The method of claim 56 or claim 57 wherein the copolymer has a number average molecular weight of from 1,000 to 120,000.

72. The method of claim 56 or claim 57 wherein the solvent comprises a component solvent miscible with the solvent.

73. The method of claim 72 wherein the component solvent is selected from the group consisting of triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one, and mixtures thereof.

74. The method of claim 72 wherein the component solvent is selected from the group consisting of triacetin and N-methyl-2-pyrrolidone, and mixtures thereof.

75. The method of claim 72 wherein the component solvent is triacetin.

76. The method of claim 56 or claim 57 wherein the beneficial agent is present in an amount of from 1 to 50% by weight of the combined amounts of the polymer, the solvent, and the beneficial agent.

77. The method of claim 56 or claim 57 wherein the beneficial agent is cDNA, DNA, a protein, a peptide, and derivatives or fragments thereof, or a chemotherapeutic agent.

78. The method of claim 56 or claim 57 wherein the beneficial agent is human growth hormone, methionine-human growth hormone, des-phenylalanine human growth hormone, interferon alpha-2$a$, interferon alpha-2b, or consensus interferon.

79. The method of claim 56 or claim 57 wherein the solvent is ethyl benzoate.

80. The method of claim 56 or claim 57 wherein the system is non-rigid after implantation.

81. The method of claim 80 wherein the system maintains a glass transition temperature below 37° C. for at least 24 hours after implantation.

* * * * *